(12) United States Patent
Frenken et al.

(10) Patent No.: US 8,105,592 B2
(45) Date of Patent: Jan. 31, 2012

(54) HEAVY CHAIN AND SINGLE DOMAIN ANTIBODIES

(75) Inventors: Leo Gerardus Joseph Frenken, Vlaardingen (NL); Lars-Göran Lennart Hammarström, Huddinge (SE); Adrianus Marinus Ledeboer, Vlaardingen (NL)

(73) Assignee: VHsquared Limited, Birmingham (GB)

( * ) Notice: Subject to any disclaimer, the term of this patent is extended or adjusted under 35 U.S.C. 154(b) by 213 days.

(21) Appl. No.: 11/791,456

(22) PCT Filed: Nov. 3, 2005

(86) PCT No.: PCT/EP2005/011805
§ 371 (c)(1),
(2), (4) Date: Mar. 7, 2008

(87) PCT Pub. No.: WO2006/056306
PCT Pub. Date: Jun. 1, 2006

(65) Prior Publication Data
US 2008/0206233 A1 Aug. 28, 2008

(30) Foreign Application Priority Data

Nov. 25, 2004 (EP) .................................... 04078211
Nov. 25, 2004 (EP) .................................... 04078212

(51) Int. Cl.
*A61K 35/66* (2006.01)
*A61K 39/395* (2006.01)
(52) U.S. Cl. .................. 424/133.1; 424/93.2; 435/252.5
(58) Field of Classification Search .................. 424/93.2; 424/133.1; 435/252.5
See application file for complete search history.

(56) References Cited

FOREIGN PATENT DOCUMENTS

| DE | 3735777 | 5/1989 |
|---|---|---|
| EP | 0739981 | 10/1996 |
| EP | 1134231 | 9/2001 |
| WO | WO 99/46300 | 9/1999 |
| WO | WO 00/06764 | 2/2000 |
| WO | WO 00/65057 | 11/2000 |
| WO | 2004/003019 | * 1/2004 |

OTHER PUBLICATIONS

International Search Report from PCT/EP2005/011805 (Aug. 25, 2006; pp. 1-5).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Lederman et al (Molecular Immunology 28:1171-1181, 1991).*
Li et al (Proc. Natl. Acad. Sci. USA 77:3211-3214, 1980).*
Baek et al. "Expression and secretion of carboxymethyl cellulase in *Bacillus subtilis* by *Lactobacillus casei* lactate dehydrogenase gene promoter", Biotechnology Letters, 19(1), pp. 27-29 (1997).
Krüger et al. "In situ delivery of passive immunity by lactobacilli producing single-chain antibodies", Nat. Biotechnol., 20, pp. 702-706 (2002).
Reilly et al. "Oral delivery of antibodies. Future pharmacokinetic trends", Clin. Pharmacokinet, 32(4), pp. 313-323 (1997).

* cited by examiner

*Primary Examiner* — Lynn Bristol
(74) *Attorney, Agent, or Firm* — Morgan, Lewis & Bockius LLP

(57) ABSTRACT

The present invention relates to heavy chain immunoglobulins or fragments thereof of the VHH or VNAR type, or domain antibodies (dAbs) of the heavy or light chains of immunoglobulins or fragments thereof, suitable for use in the management of infections, in particular of the gastrointestinal tract. The present invention also relates to a delivery system comprising these heavy chain immunoglobulins or functional fragments thereof of the VHH or VNAR type, or domain antibodies (dAbs) of the heavy or light chains of immunoglobulins or fragments thereof, and hosts comprising expression vectors encoding for these heavy chain immunoglobulins or functional fragments thereof of the VHH or VNAR type, or domain antibodies (dAbs) of the heavy or light chains of immunoglobulins or fragments thereof. The invention also relates to food products and pharmaceutical preparations comprising the delivery system, and methods for the preparation of food products according to the invention.

17 Claims, 10 Drawing Sheets

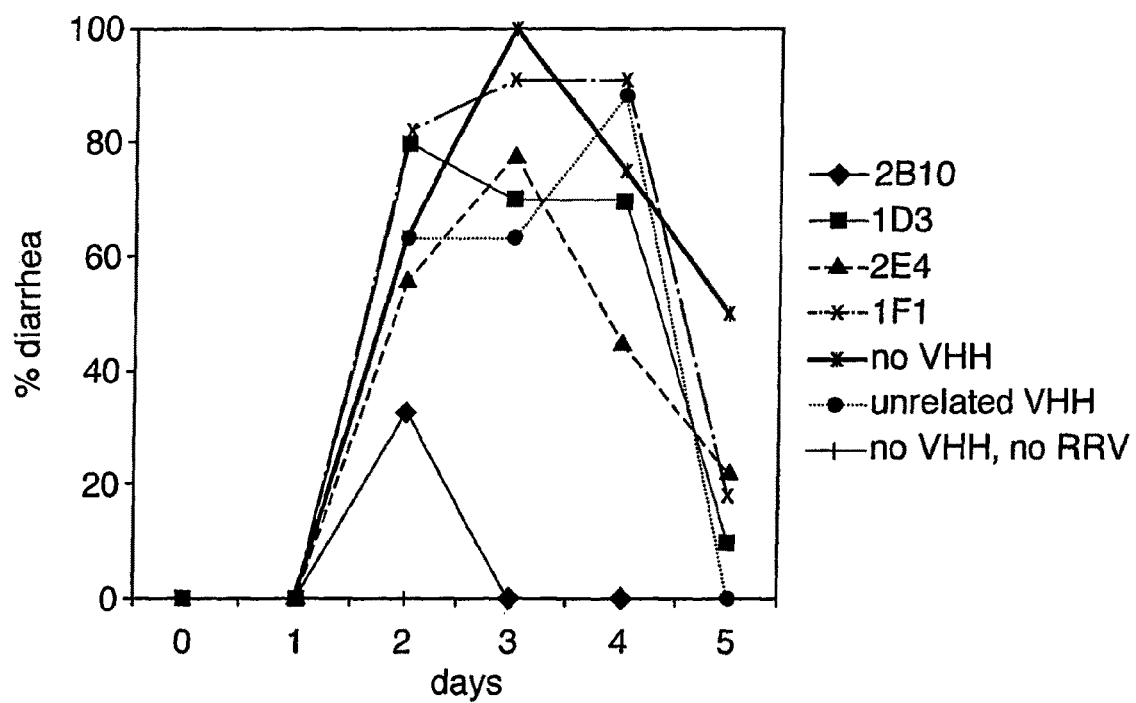

HEAVY CHAIN AND SINGLE DOMAIN ANTIBODIES

RELATED APPLICATIONS

The present application is a U.S. National Phase Application of International Application No. PCT/EP2005/011805, filed Nov. 3, 2005, which claims the benefit of EP Patent Application No. 04078212.0, filed Nov. 25, 2004, and EP Patent Application No. 04078211.2, filed Nov. 25, 2004, all of which are hereby incorporated by reference in their entirety.

SEQUENCE LISTING

A computer readable text file, entitled "056159-5264-SequenceListing.txt," created on or about Jul. 14, 2010 with a file size of about 24 kb contains the sequence listing for this application and is hereby incorporated by reference in its entirety.

FIELD OF THE INVENTION

The present invention relates to heavy chain immunoglobulins of the VHH or VNAR type or domain antibodies (dAbs) of the heavy or light chains of immunoglobulins or fragments thereof suitable for use in the management of infections by enteropathogenic micro-organisms. The present invention also relates to a delivery system comprising these heavy chain immunoglobulins of the VHH or VNAR type or domain antibodies (dAbs) of the heavy or light chains of immunoglobulins or fragments thereof, and hosts comprising expression vectors encoding for these heavy chain immunoglobulins of the VHH or VNAR type or domain antibodies (dAbs) of the heavy or light chains of immunoglobulins or fragments thereof. The invention further relates to food products or pharmaceutical preparations comprising a delivery system for delivering antibodies to the gastro-intestinal tract (GIT) wherein the antibodies are active in the gut.

BACKGROUND OF THE INVENTION

Immunoglobulins (also called antibodies) are glycoproteins, which specifically recognise foreign molecules. These recognised foreign molecules are called antigens. When antigens invade humans or animals, an immunological response is triggered which involves the production of antibodies by B-lymphocytes. By this immunological response, microorganisms, larger parasites, viruses and bacterial toxins can be rendered harmless. The unique ability of antibodies to specifically recognise and bind with high affinity to virtually any type of antigen, makes them useful molecules in medical and scientific research.

In vertebrates five immunoglobulin classes are described, including IgG, IgM, IgA, IgD and IgE, all of which differ in their function in the immune system. IgGs are the most abundant immunoglobulins in the blood. They have a basic structure of two identical heavy (H) chain polypeptides and two identical light (L) chain polypeptides. The H and L chains are kept together by disulfide bridges and non-covalent bonds. The chains themselves can be divided in variable and constant domains. The variable domains of the heavy and light chain (VH and VL) which are extremely variable in amino acid sequences are located at the N-terminal part of the antibody molecule. VH and VL together form the unique antigen-recognition site. The amino acid sequences of the remaining C-terminal domains are much less variable and are called CH1, CH2, CH3 and CL.

The non-antigen binding part of an antibody molecule is called the constant domain Fc and mediates several immunological functions, such as binding to receptors on target cells and complement fixation. The unique antigen-binding site of an antibody consists of the heavy and light chain variable domains (VH and VL). Each domain contains four framework regions (FR) and three regions called CDRs (complementarity determining regions) or hypervariable regions. The CDRs strongly vary in sequence and determine the specificity of the antibody. VL and VH domains together form a binding site, which binds a specific antigen.

Several functional antigen-binding antibody fragments could be engineered by proteolysis of antibodies, using for example papain digestion, pepsin digestions or other enzymatic approaches. Such a technique can be used to yield Fab, Fv or single domain fragments. Fab fragments are the antigen-binding domains of an antibody molecule. Fab fragments can be prepared by papain digestions of whole antibodies. Fv fragments are the minimal fragment (~30 kDa) that still contains the whole antigen-binding site of a whole IgG antibody. Fv fragments are composed of both the variable heavy chain (VH) and variable light chain (VL) domains. This heterodimer, called Fv fragment (for fragment variable) is still capable of binding the antigen.

Heavy chain antibodies constitute about one fourth of the IgG antibodies produced by the camelids, e.g. camels and llamas (Hamers-Casterman C., et al. (1993)). These antibodies are formed by two heavy chains but are devoid of light chains. As a consequence, the variable antigen binding part is referred to as the VHH domain and it represents the smallest naturally occurring, intact, antigen-binding site, being only around 120 amino acids in length (Desmyter, A., et al. (2001)). Heavy chain antibodies with a high specificity and affinity can be generated against a variety of antigens through immunization (van der Linden, R. H., et al. (1999)) and the VHH portion can be readily cloned and expressed in yeast (Frenken, L. G. J., et al. (2000)). Their levels of expression, solubility and stability are significantly higher than those of classical F(ab) or Fv fragments (Ghahroudi, M. A. et al. (1997)). Sharks have also been shown to have a single VH-like domain in their antibodies termed VNAR. (Nuttall et al. (2003)); (Dooley et al. (2003)); (Nuttall et al. (2004)).

Holt et al. (2003) reviews antigen-binding fragments called "domain antibodies" or dAbs which comprise only the VH or VL domain of an antibody and are consequently smaller than, for example, Fab and scFv. DAbs are the smallest known antigen-binding fragments of antibodies, ranging from 11 kDa to 15 kDa. They are highly expressed in microbial cell culture. Each dAb contains three of the six naturally occurring complementarity determining regions (CDRs) from an antibody.

The production of antibodies for use in conventional immunotherapy has been possible since the development of monoclonal antibody technology. This has led to the use of antibodies in many areas including research, medicine and recently in consumer applications.

Unfortunately, there are many problems associated with conventional immunotherapy. Such applications rely on the large scale production of antibodies and involve the use of the antibody or antibody fragment per se, that is the harvested protein from, for example, an antibody expression system. Thus, the associated production costs, including the requirement for purification of the antibodies before administration, are expensive and make their wide scale application as immunotherapeutics prohibitive. Furthermore, in order to treat a large part of the population, large amounts of conventional immunotherapy products would be required. If, for example, the therapy was based on colostrum and/or immunised chicken eggs, it would be difficult to provide the required amounts of the immunotherapy products in a large volume.

Furthermore, in a recent article, "In situ delivery of passive immunity by *lactobacilli* producing single-chain antibodies" Nature Biotechnol. (2002) 20, 702-706, Kruger et al reported on the production of scFv antibody fragments against *Streptococcus mutans* by the Gram positive food grade bacteria *Lactobacillus zeae*. This treatment involved in situ delivery of passive immunity at oral mucosal sites only wherein the single chain antibody fragments were shown to deliver protection against dental caries in rats.

*Lactobacilli* have been investigated with regards to their anti-diarrhoeal properties since the 1960's (Beck, C., et al. Beneficial effects of administration of *Lactobacillus acidophilus* in diarrhoeal and other intestinal disorders. Am. J. Gastroenterol (1961) 35, 522-30). A limited number of recent controlled trials have shown that certain strains of *lactobacilli* may have therapeutic as well as prophylactic properties in acute viral gastroenteritis (Mastretta, E., et al. Effect of *Lactobacillus* CG and breast-feeding in the prevention of rotavirus nosocomial infection. J. Pediatr. Gastroenterol. Nutr. (2002) 35, 527-531). Selected strains of *Lactobacillus casei* and *Lactobacillus plantarum* have also been shown to exert strong adjuvant effects on the mucosal and the systemic immune response. *Lactobacilli* are well-known bacteria applied in the production of food products. For example yogurt is normally made by fermenting milk with among others a *Lactobacillus* strain. The fermented acidified product, still containing the viable *Lactobacillus*, is then cooled and consumed at the desired moment.

Another application of *Lactobacillus* in food products is in the production of meat products for example sausages. Here the *Lactobacillus* is added to the meat mass prior to applying the casing, followed by a period of ripening in which the fermentation process takes place.

Still another application of *Lactobacillus* in the production of food products is the brining of vegetables such as cabbage (sauerkraut), carrots, olives or beets. Here the natural fermentation process can be controlled by the addition of an appropriate *Lactobacillus* starter culture.

The application of *Lactobacillus* in food products is often associated with several health effects, see for example A. C. Ouwehand et al. in Int. Dairy Journal 8 (1998) 749-758. In particular the application of products is associated with several health effects for example relating to gut well being such as IBS (Irritable Bowel Syndrome), reduction of lactose maldigestion, clinical symptoms of diarrhoea, immune stimulation, anti-tumour activity and enhancement of mineral uptake.

WO 99/23221 discloses multivalent antigen binding proteins for inactivating phages. The hosts may be lactic acid bacteria which are used to produce antibody binding fragments which are then harvested and used. WO 99/23211 discloses adding the harvested antibody fragments to provide anti-diarrhea effects.

WO 00/65057 is directed to the inhibition of viral infection using monovalent antigen-binding proteins. The antigen-binding protein may be a heavy chain variable domain derived from an immunoglobulin naturally devoid of light chains, such as those derived from Camelids as described in WO 94/04678. WO 00/65057 discloses transforming a host with a gene encoding the monovalent antigen-binding proteins. Suitable hosts can include lactic acid bacteria. This disclosure relates to the field of fermentation processing and the problem of phage infection which hampers fermentation.

Specifically, llama VHH fragments per se are used to solve the problem of phage infection by neutralising *Lactoccocus lactis* bacteriophage P2.

Both WO 00/65057 and WO 99/23221 involve the use of antibody fragments harvested from a bacterial expression system.

U.S. Pat. No. 6,605,286 is directed to the use of gram positive bacteria to deliver biologically active polypeptides, such as cytokines, to the body. U.S. Pat. No. 6,190,662 and EP 0 848 756 B1 are directed to methods for obtaining surface expression of a desired protein or polypeptide. Monedero et al 2004 is directed to in-vitro studies on the use of single-chain antibodies (scFv) expressed by *L. casei* which recognise the VP8 and fraction of rotavirus outer capsid and blocks rotavirus infection in vitro. However, none of these documents disclose the use of heavy chain immunoglobulins or fragments of the VHH or VNAR type or domain antibodies.

One major disadvantage of these known systems is that the use of antibodies or antibody fragments per se (i.e. a harvested protein) in the treatment of a disease in a human may result in the antibody being degraded or digested before they provide the desired health benefits and even before they reach the desired location. Furthermore, it is often desirable to ensure that the antibody or antibody fragments are active in a specific region of the body. This will depend on the particular infection being treated.

Enteropathogenic micro-organisms are micro-organisms which can produce disease in the intestinal tract. Examples of such micro-organisms include *E. coli* and *Salmonella*.

Another example of an enteropathogen is rotavirus. Rotavirus continues to be the single most common cause of infantile diarrhoea in the world and most children get infected during the first 5 years of life. In developing countries, rotavirus induced diarrhoea may cause 600,000 to 870,000 deaths each year and in developed countries, rotavirus disease accounts for immense economic loss. Following the intussusception related withdrawal of the Rhesus rotavirus-tetravalent vaccine in July 1999, several strategies have been employed to try to develop a safe vaccine. Five oral live attenuated rotavirus vaccines are presently undergoing clinical trials for use in children, for example Barnes, G. L. et al. (1997). However, in particular in very young, malnourished children in developing countries the efficacy of such vaccinations might be limited. Several studies have also been conducted using passive immunotherapy, for example Offit, P. A. et al. (1985).

Secretory immunoglobulins are implicated as a first line of defense against many mucosal pathogens, including rotavirus infection. Protection from clinical disease appears to rely mainly on the production of neutralizing antibodies against the outer capsid proteins VP4 or VP7 (Ruggeri, F. M. at al. (1998)); (Giammarioli, A-M. et al. (1996)). Recently however, non-neutralizing VP6 specific IgA antibodies have also been shown to inhibit rotavirus replication (Feng, N. et al. (2002)); Schwartz-Cornil, I. et al. (2002)). Both hyperimmune bovine colostrum and chicken egg yolks derived antibodies have previously been shown to be effective in the treatment of rotavirus diarrhoea (Davidson et al. (1989)); (Sarker, S. A., et al. (2001)). Successful treatment of rotavirus diarrhoea in children with immunoglobulin from immunized bovine colostrums has also been demonstrated (Sarker S. A. et al. (1998)). However, the high costs of production of these immunoglobulin preparations make their wide scale application as immunotherapeutics prohibitive.

To date, no specific therapy is available for the widespread management of enteropathogenic micro-organisms and viruses. For example, the current management of rotavirus induced diarrhoea mainly involves prevention and oral rehydration. Thus, it is desirable to provide an alternative means for the management of enteropathogenic micro-organisms, by therapy and/or prophylaxis.

The present invention is directed to a new method of therapy and/or prophylaxis of enteropathogenic micro-organisms.

REFERENCES

Acedo-Félix, E., & Pérez-Martínez, G. Significant differences between *Lactobacillus casei* subsp. *casei* ATCC 393T and commonly used plasmid-cured derivative revealed by a polyphasic study. Int. J. System. Evol. Microbiol. 53, 67-75 (2003).

Barnes, G. L. et al. Phase I trial of a candidate rotavirus vaccine (RV3) derived from a human neonate. J. Paediatr. Child Health. 33, 300-304 (1997).

Beck, C., et al. Beneficial effects of administration of *Lactobacillus acidophilus* in diarrhoeal and other intestinal disorders. Am. J. Gastroenterol. 35, 522-530 (1961).

Bernstein, D., et al. Efficacy of live, attenuated, human rotavirus vaccine 89-12 in infants: a randomised placebo-controlled trial. Lancet. 354, 287-290 (1999).

Boshuizen J A, Reimerink J H, Korteland-van Male A M, van Ham V J, Koopmans M P, Buller H A, Dekker J, Einerhand A W. Changes in small intestinal homeostasis, morphology, and gene expression during rotavirus infection of infant mice. J Virol. 77, 13005-16 (2003).

Clemens-Mann, M-L., et al. Safety and immunogenicity of live attenuated human-bovine (UK) reassortant rotavirus vaccines with VP7-specificity for serotypes 1, 2, 3 or 4 in adults, children and infants. Vaccine. 17, 2715-2725 (1999).

Cook, S. M. et al. Global seasonality of rotavirus infections. Bull WHO. 68, 171-177 (1990).

Davidson et al., "Passive immunisation of children with bovine colostrum containing antibodies to human rotavirus" Lancet (1989) 334:709-712.

Desmyter, A., Decanniere, K., Muyldermans, S., & Wyns, L. Antigen specificity and high affinity binding provided by one single loop of a camel single-domain antibody. J. Biol. Chem. 276, 26285-26290 (2001).

Dooley et al. "Selection and characterization of naturally occurring single-domain (IgNAR) antibody fragments from immunized sharks by phage display" Molecular Immunology (2003) 40, 25-33.

Feng, N. et al. Inhibition of rotavirus replication by a non-neutralizing rotavirus VP6-specific IgA mAb. J. Clin. Invest. 109, 1203-1213 (2002).

Frenken, L. G. J., et al. Isolation of antigen specific Llama VHH antibody fragments and their high level secretion by *Saccharomyces cerevisiae*. J. Biotechnol. 78, 11-21 (2000).

Ghahroudi, M. A., Desmyter, A., Wyns, L., Hamers, R. & Muyldermans S. Selection and identification of single domain antibody fragments from camel heavy-chain antibodies. FEBS Lett. 414, 521-526 (1997).

Giammarioli, A-M., Mackow, E. R., Fiore, L., Greenberg, H. B. & Ruggeri, F. M. Production and characterization of murine IgA monoclonal antibodies to the surface antigens of rhesus rotavirus. Virol. 225, 97-110 (1996).

Guarino, A. et al. Enteral immunoglobulins for treatment of protracted rotaviral diarrhoea. Pediatr. Infect. Dis. J. 10, 612-614 (1991).

Hamers-Casterman C., et al. Naturally occurring antibodies devoid of light-chains. Nature. 363, 446-448 (1993).

Holt, L. J. et al. Domain antibodies: proteins for therapy. Trends in Biotechnology (2003) Vol. 21, No. 11: 484-490.

Isolauri, E., Joensuu, J., Soumalainen, H., Luomala, M. & Vesikari, T. Improved immunogenicity of oral D x RRV reassortant rotavirus vaccine by *Lactobacillus casei* GG. Vaccine. 13, 310-312 (1995).

Kirkwood, C. D., Jim Buttery. Rotavirus vaccines—an update, Expert Opin Biol Ther. 3(1), 97-105 (2003).

Krüger, C., et al. In situ delivery of passive immunity by lactobacilli producing single-chain antibodies. Nature Biotechnol. 20, 702-706 (2002).

Krüger, C., Hultberg, A., Marcotte, H., Hermans, P., Frenken, L. G. J. & Hammarström, L. Passive immunization against caries using llama derived VHH fragments against *Streptococcus mutans*. (submitted)

Nuttall et al. "Isolation and characterization of an IgNAR variable domain specific for the human mitochondrial translocase receptor Tom70" Eur. J. Biochem. (2003) 270, 3543-3554.

Nuttall et al. "Selection and affinity maturation of IgNAR variable domains targeting *Plasmodium falciparum* AMA1" Proteins: Structure, Function and Bioinformatics (2004) 55, 187-197).

Ma, J. K., Smith, C. R., & Lehner, T. Use of monoclonal antibodies in local passive immunization to prevent colonization of human teeth by *Streptococcus mutans*. Infect Immun. 55, 1274-1278 (1987).

Maassen, C. B., et al. Instruments for oral disease-intervention strategies: recombinant *Lactobacillus casei* expressing tetanus toxin fragment C for vaccination or myelin proteins for oral tolerance induction in multiple sclerosis. Vaccine. 17, 2117-2128 (1999).

Mastretta, E., et al. Effect of *Lactobacillus* GG and breast-feeding in the prevention of rotavirus nosocomial infection. J. Pediatr. Gastroenterol. Nutr. 35, 527-531 (2002).

Mondero et al. Selection of single-chain antibodies against the VP8 Subunit of rotavirus VP4 outer capsid protein and their expression in *L. casei*. Applied and Environmental Microbiology No. 4 (2004) 6936-6939.

Offit, P. A. et al. Protection against rotavirus-induced gastroenteritis in a murine model by passively acquired gastrointestinal but not circulating antibodies. J. Virol. 54, 58-64 (1985).

Overbergh L, Valckx D, Waer M, Mathieu C. Quantification of murine cytokine mRNAs using real time quantitative reverse transcriptase PCR. Cytokine. 11, 305-312 (1999).

Parashar, U. D., Hummelman, E. G., Bresee, J. S., Miller, M. A., Glass, R I. Global illness and deaths caused by rotavirus disease in children. Emerg. Infect. Dis. 9, 565-572 (2003).

Perdigon, G., de Marcias, M. E., Alvarez, S., Oliver, G. & de Ruiz Holgado, A. P. Systemic augmentation of the immune response in mice by feeding fermented milks with *Lactobacillus casei* and *Lactobacillus acidophilus*. Immunology. 63, 17-23 (1988).

Pouwels, P. H., Leer, R. J. & Boersma, W. J. The potential of *Lactobacillus* as a carrier for oral immunization: development and preliminary characterization of vector systems for targeted delivery of antigens. J. Biotechnol. 44, 183-192 (1996).

Ruggeri, F. M., Johansen, K., Basile, G., Kraehenbuhl, J-P. & Svensson, L. Antirotavirus Inmunoglobulin A neutralizes virus in vitro after transcytosis through epithelial cells and protects infant mice from diarrhoea. J. Virol. 72, 2708-2714 (1998).

Sarker, S. A., et al. Successful treatment of rotavirus diarrhoea in children with immunoglobulin from immunized bovine colostrum. Pediatr. Infect. Dis. J. 17, 1149-1154 (1998).

Sarker, S. A., et al. Randomized, placebo-controlled, clinical trial of hyperimmunized chicken egg yolk immunoglobulin in children with rotavirus diarrhoea. J. Pediatr. Gastroenterol. Nutr. 32, 19-25 (2001).

Schwartz-Cornil, I., Benureau, Y., Greenberg, H., Hendrickson, B. A. & Cohen, J. Heterologous protection induced by the inner capsid proteins of rotavirus requires transcytosis of mucosal immunoglobulins. J. Virol. 76, 8110-8117 (2002).

Svensson, L., Finlay, B. B., Bass, D., von Bonsdorff, C. H. & Greenberg, H. B. Symmetric infection of rotavirus on polarized human intestinal epithelial (Caco-2) cells. J. Virol. 65, 4190-4197 (1991).

van der Linden, R. H. et al. Comparison of physical properties of llama VHH antibody fragments and mouse monoclonal antibodies. Biochim. Biophys. Acta. 1431, 37-46 (1999).

Weekly epidemiological record. Rotavirus vaccines. World Health Organization 74, 33-40 (1999).

Weiner, C., Pan, Q., Hurtig, M., Borén, T., Bostwick. E. & Hammarström, L. Passive immunity against human pathogens using bovine antibodies. Clin. Exp. Immunol. 116, 193-205 (1999).

Zimmerman, C. M., Bresee, J. S., Parashar, U. D., Riggs, T. L., Holman, R. C. & Glass, R. I. Cost of diarrhoea-associated hospitalizations and outpatient visits in an insured population of young children in the United States. Pediatr. Infect. Dis. J. 20, 14-19 (2001).

SUMMARY OF THE INVENTION

According to a first aspect of the invention, there is provided a delivery system for delivering antibodies to the GIT comprising heavy chain immunoglobulins or fragments thereof of the VHH or VNAR type, or domain antibodies (dAbs) of the heavy or light chains of immunoglobulins or fragments thereof, wherein the immunoglobulins or fragments thereof are active in the gut.

According to a second aspect of the invention, there is provided an expression vector comprising the gene encoding for the heavy chain immunoglobulins or fragments thereof of the VHH or VNAR type, or domain antibodies (dAbs) of the heavy or light chains of immunoglobulins or fragments thereof.

According to a third aspect, there is provided a micro-organism, preferably Lactobacillus, transformed with the above expression vector.

According to a fourth aspect, there is provided a method for delivering antibodies to the gut in the treatment of enteropathogenic micro-organism infections using a micro-organism transformed with the gene encoding for heavy chains immunoglobulins or fragments thereof of the VHH or VNAR type, or domain antibodies (dAbs) of the heavy or light chains of immunoglobulins or fragments thereof, comprising the steps of:

i) transforming the micro-organism with an expression vector comprising heavy chain immunoglobulins of the VHH or VNAR type or domain antibodies (dAbs) of the heavy or light chains of immunoglobulins or fragments thereof; and ii) administering the transformed micro-organism to the gut of the human or animal in need of therapy such that the heavy chain immunoglobulins or fragments thereof of the VHH or VNAR type, or domain antibodies (dAbs) of the heavy or light chains of immunoglobulins or fragments thereof, are expressed and/or secreted in the gut.

According to a fifth aspect of the invention, there is provided the use of heavy chain immunoglobulins or fragments thereof of the VHH or VNAR type, or domain antibodies (dAbs) of the heavy or light chains of immunoglobulins or fragments thereof, or the delivery system as described above in therapy.

According to a sixth aspect of the invention, there is provided heavy chain immunoglobulins or fragments thereof of the VHH or VNAR type, or domain antibodies (dAbs) of the heavy or light chains of immunoglobulins or fragments thereof, or the delivery system as described above in the manufacture of a medicament for the treatment of enteropathogenic micro-organism infections, preferably rotaviral infection.

Further embodiments include a food product comprising a delivery system for delivering antibodies to the GIT wherein the antibodies are active in the gut and a pharmaceutical preparation comprising a delivery system for delivering antibodies to the GIT wherein the antibodies are active in the gut and the antibodies are heavy chain immunoglobulins of the VHH or VNAR type or fragments thereof, or domain antibodies (dAbs) of the heavy or light chains of immunoglobulins or fragments thereof.

According to a another aspect of the invention, there is provided a method for making a food product or pharmaceutical preparation comprising adding the delivery system to the food product or pharmaceutical preparation during the manufacture of the food product or pharmaceutical preparation.

According to another aspect of the invention, there is provided the use of the food product or pharmaceutical preparation as described above to deliver health benefits to the gut of a subject.

BRIEF DESCRIPTION OF THE FIGURES

In the detailed description of the embodiments of the invention, reference is made to the following figures.

FIG. 2 shows that rotavirus specific VHH particles neutralise rotavirus in-vivo.

| | |
|---|---|
| Tldh: | transcription terminator of the lactate dehydrogenase gene of L. casei; |
| deleted Tld:, | remaining sequence after deletion of Tldh; |
| 2A10-scFv: | single-chain antibody against VP4/VP7; |
| VHH1: | heavy chain antibody fragment against rotavirus; long anchor, anchor sequence from the proteinase P gene of *L. casei* (244 amino acids); |
| Tcbh: | transcription terminator sequence of the conjugated bile acid hydrolase gene of *L. plantarum* 80; |
| Pldh: | Promotor sequence of the lactate dehydrogenase gene of *L. casci*, SS |
| PrtP; | signal sequence of the PrtP gene (33 aa), N-terminus PrtP, N-terminus (36 amino cids) of the PrtP gene; |
| Ampr: | ampicillin-resistance gene; |
| Ery: | erythromycin-resistance gene; |
| Rep: | repA gene of plasmid p353-2 from *L. pentosis*; |
| Ori: | origin of replication (Ori+ = ori *E. coli*, Ori– = ori *Lactobacillus*). |
| Arrows: | indicate a stop codon. |

Figure 4A:
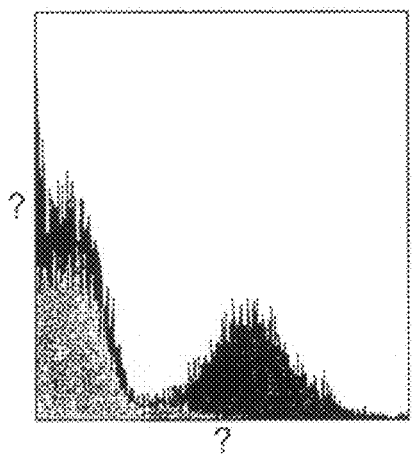

FIG. 4a shows the results of Flow cytometry showing the expression of 2A10-scFv (light grey) and VHH1 (dark grey) on the surface of the *Lactobacillus paracasei* by detection of the E-tag by a mouse anti-E-tag antibody (b) Scanning electron microscope (SEM) picture showing the binding of rotavirus by the VHH1 surface expressing *Lactobacillus paracasei*.

Figure 5:
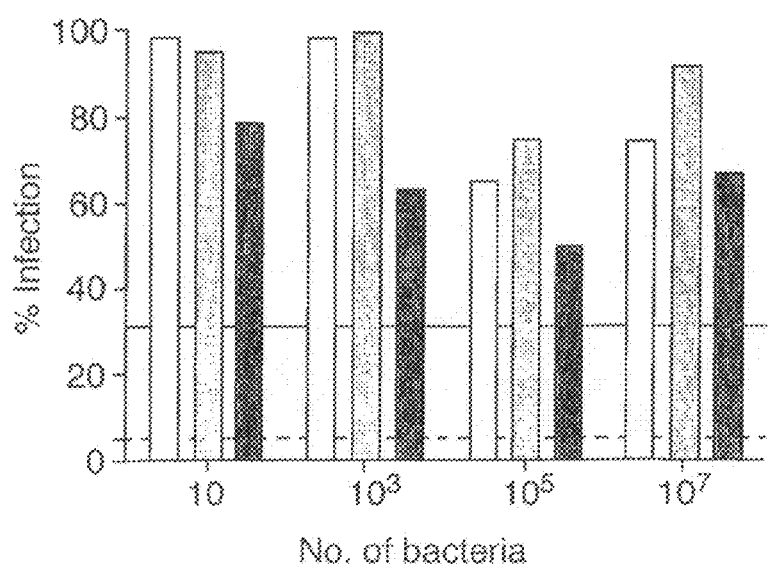

FIG. 5 shows in vitro neutralization assay results which test efficacy of *lactobacilli* expressing VHH1-anchored fragments to inhibit rotavirus infection of MA104 cells. Reduction of infection to 60% or more was considered to be specific neutralization. The solid line represents neutralization level achieved by *lactobacilli* produced E-tag purified VHH1 antibody (20 µg/ml). Dotted line indicates the neutralization level of 2A10 monoclonal hybridoma supernatant (147 ng/ml). Neutralization achieved by different concentrations of VHH1 anchored *lactobacilli* (■), 2A10 anchored *lactobacilli* (( )) and non-transformed *lactobacilli* (☐).

Figure 6A:
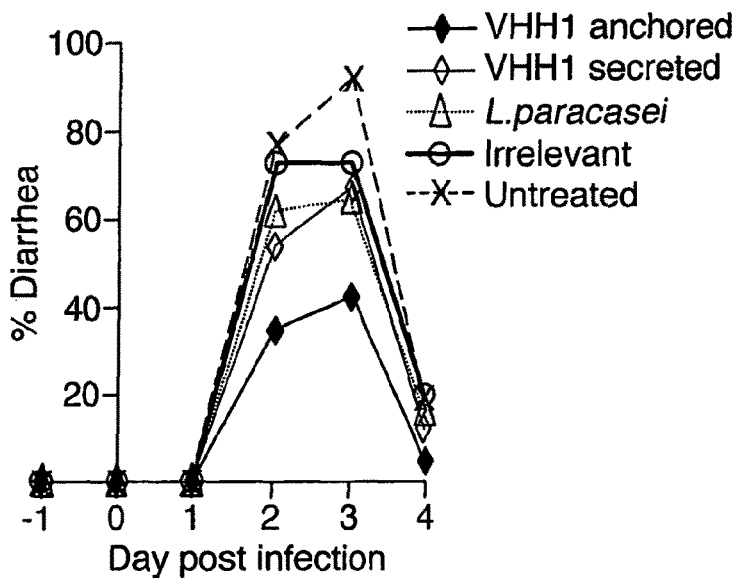

FIG. 6(a) shows the prevalence of diarrhoea in mice treated with *lactobacilli* expressing VHH1-anchored fragments. Pooled results of three experiments (b) Prevalence of diarrhoea in mice treated with *lactobaccili* surface expressing 2A10-scFv. Pooled results from three experiments.

FIG. 7 shows duodenum and jejunum sections from pups treated with different formulations, stained with hematoxylin and eosin. The bar represents 100 µm length.

Figure 8:
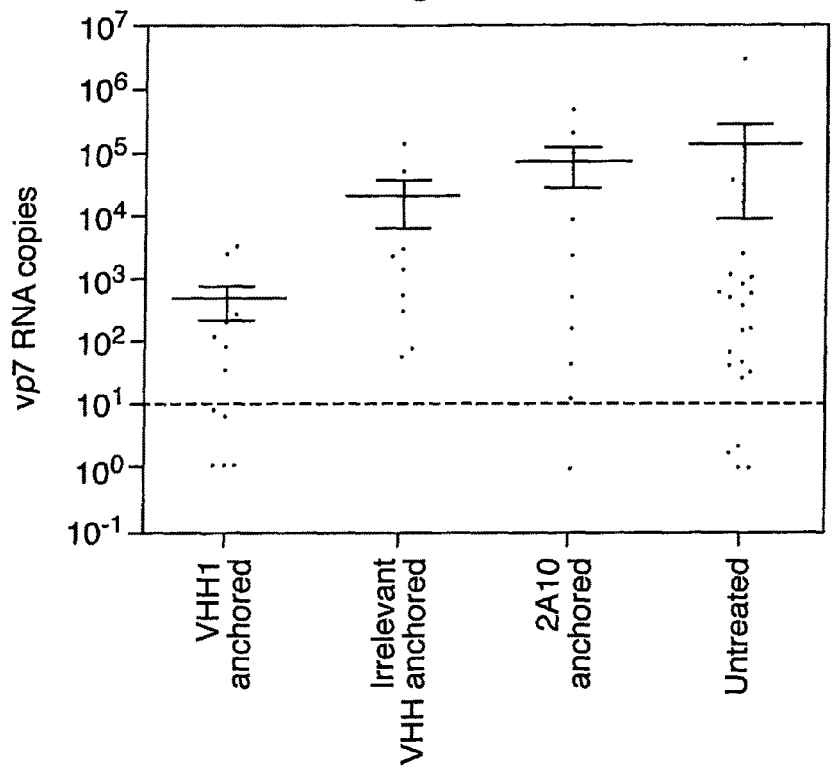

FIG. 8 shows the load of vp7 RNA in small intestinal tissue samples as determined by real time PCR.

Figure 9:
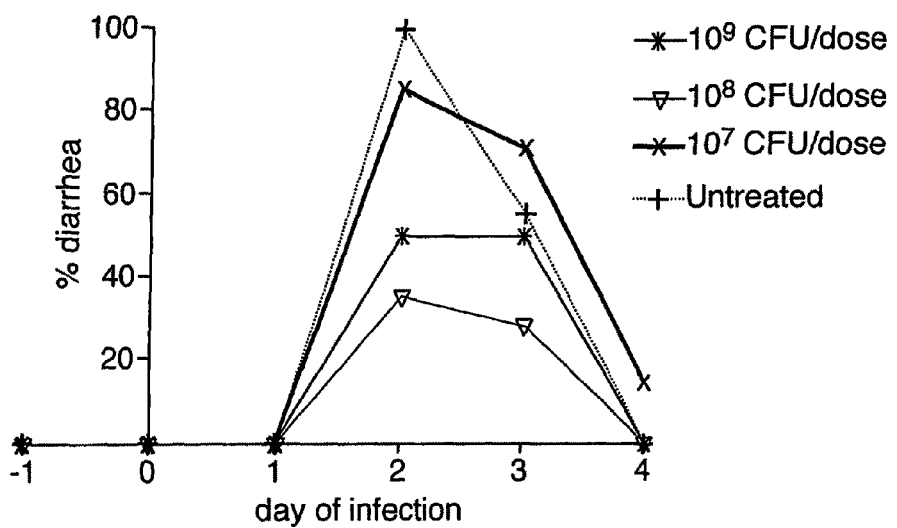

FIG. 9 shows evaluation of different doses of *lactobacilli* expressing VHH1-anchored fragments and their efficacy to reduce diarrhea.

Figure 10:
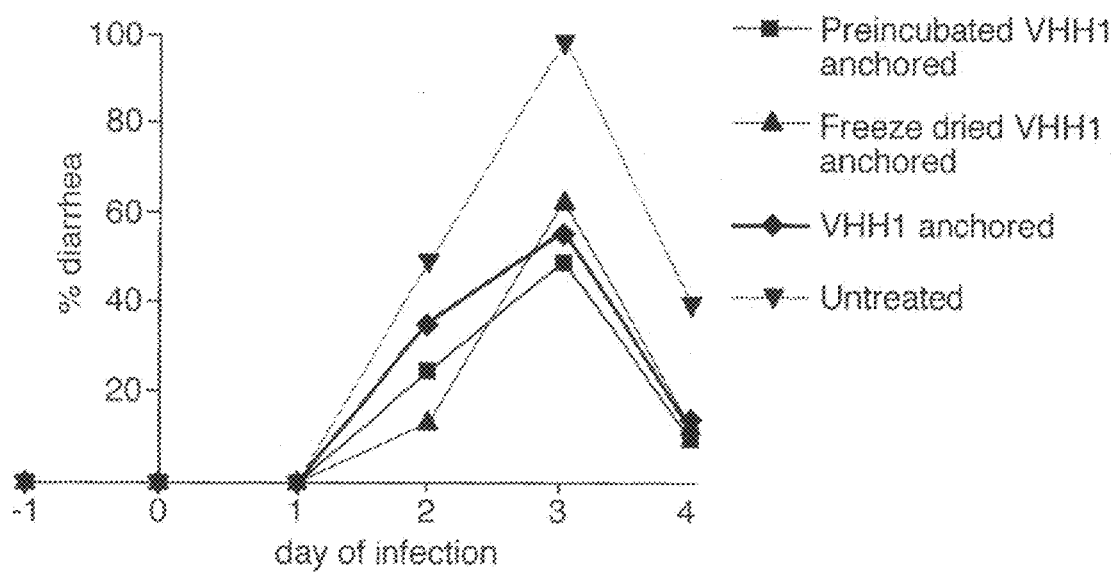

FIG. 10 shows evaluation of *lactobacilli* expressing VHH1-anchored fragments in a freeze-dried form.

FIG. 11 shows scanning electron microscope (SEM) picture showing the binding of rotavirus by the VHH1 surface expressing *Lactobacillus paracasei*.

Figure 12:
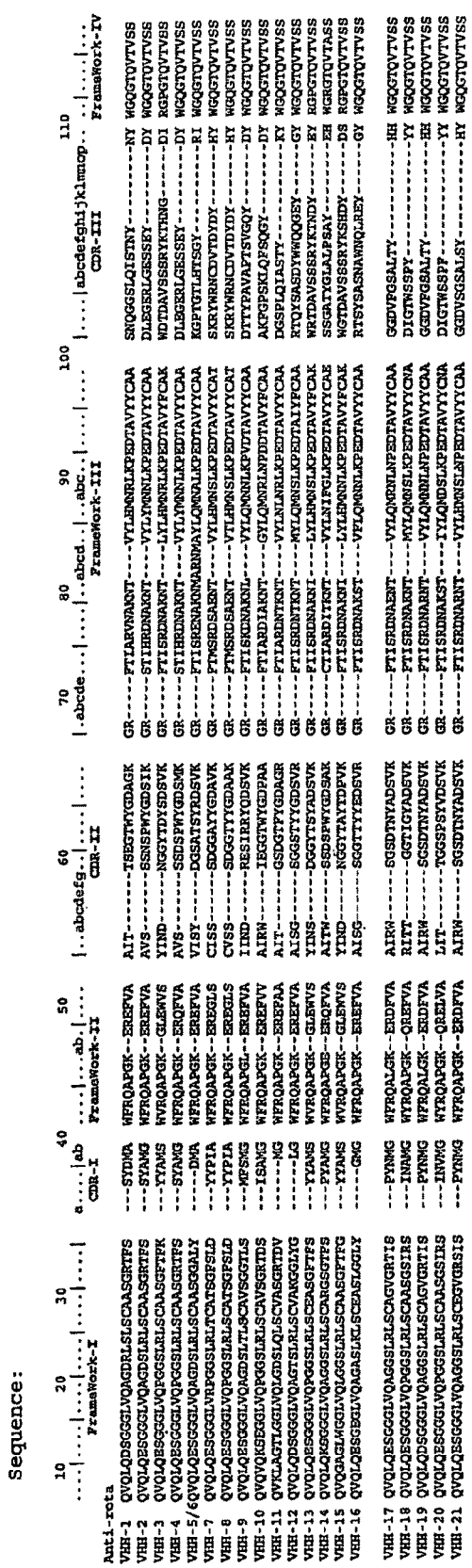

FIG. 12 shows an alignment of the VHH's having affinity for Rotavirus viral particles (SEQ ID NOs:1-21).

DETAILED DESCRIPTION OF THE INVENTION

The invention will now be described by way of example, by a series of embodiments.

In general, the present invention is directed to the delivery of heavy chain immunoglobulins or fragments thereof of the VHH or VNAR type, or domain antibodies (dAbs) of the heavy or light chains of immunoglobulins or fragments thereof, to the gastro-intestinal tract (GIT) which are suitable for use in the management of infection by enteropathogenic micro-organisms.

The present invention is also directed to a food product or pharmaceutical composition comprising a delivery system for delivering antibodies to the GIT wherein the antibodies are active in the gut.

Heavy chain immunoglobulins or fragments thereof of the VHH or VNAR type, or domain antibodies (dAbs) of the heavy or light chains of immunoglobulins or fragments thereof, may be obtained using techniques well known in the art. Preferably, the immunoglobulins or fragments thereof have the following characteristics:

i) They show good binding affinity and the desired inhibition functionality under the conditions present in the GIT; and ii) They have good proteolytic stability in that they are stable against degradation by proteolytic enzymes.

Preferably, the heavy chain immunoglobulin or fragments thereof of the VHH or VNAR type, or domain antibodies (dAbs) of the heavy or light chains of immunoglobulins or fragments thereof, are specific to an enteropathogenic microorganism.

Van der Linden, R. H., et al. "Comparison of physical properties of llama VHH antibody fragments and mouse monoclonal antibodies" Biochim. Biophys. Acta (1990) 1431, 37-46 obtained heavy chain antibodies with a high specificity and affinity against a variety of antigens. Furthermore, heavy chain immunoglobulins are readily cloned and expressed in bacteria and yeast as shown in Frenken, L. G. J., et al. "Isolation of antigen specific Llama VHH antibody fragments and their high level secretion by *Saccharomyces cerevisiae*". J. Biotechnol. (2000) 78, 11-21. Methods for the preparation of such immunoglobulins or fragments thereof on a large scale comprising transforming a mould or a yeast with an expressible DNA sequence encoding the antibody or fragment are also described in WO 94/25591 in the name of Unilever. Finally, EP-A-0584421 describes heavy chain immunoglobulin regions obtained from Camelids. Nuttal et al. (2003 and 2004) and Dooley et al. (2003) describe the isolation of various VNAR antibodies. Holt et al. (2003) describes the isolation and characteristics of domain antibodies (dAbs) which have similar properties to VHH immunoglobulins.

Preferably, the antibodies may be llama heavy chain antibodies, more preferably VHH antibodies or fragments thereof. In 1993, Hamers-Casterman et al. discovered a novel class of IgG antibodies in Camelidae i.e. camels, dromedaries and llamas. ("Naturally occurring antibodies of devoid light-chains" Nature (1993) 363, 446-448). Heavy chain antibodies constitute about one fourth of the IgG antibodies produced by the camelids, llamas. These antibodies are formed by two heavy chains but are devoid of light chains. The variable antigen binding part is referred to as the VHH domain and it represents the smallest naturally occurring, intact, antigen-binding site (Desmyter, A., et al. "Antigen specificity and high affinity binding provided by one single loop of a camel single-domain antibody" J. Biol. Chem. (2001) 276, 26285-26290). Heavy chain antibodies with a high specificity and affinity can be generated against a variety of antigens and they are readily cloned and expressed in bacteria and yeast (Frenken, L. G. J., et al. "Isolation of antigen specific Llama VHH antibody fragments and their high level secretion by *Saccharomyces cerevisiae*". J. Biotechnol. (2000) 78, 11-21). Their levels of expression, solubility and stability are significantly higher than those of classical F(ab) or Fv fragments (Ghahroudi, M. A. et al "Selection and identification of single domain antibody fragments from camel heavy-chain antibodies" FEBS Lett. (1997) 414, 521-526).

Another good source of heavy chain antibodies can be found in sharks. It recently has been shown that sharks also have a single VH-like domain in their antibodies termed VNAR (Nuttall et al. "Isolation and characterization of an IgNAR variable domain specific for the human mitochondrial translocase receptor Tom70" Eur. J. Biochem. (2003) 270, 3543-3554; Dooley et al. "Selection and characterization of naturally occurring single-domain (IgNAR) antibody fragments from immunized sharks by phage display" Molecular Immunology (2003) 40, 25-33; Nuttall et al. "Selection and affinity maturation of IgNAR variable domains targeting *Plasmodium falciparum* AMA1" Proteins: Structure, Function and Bioinformatics (2004) 55, 187-197). Fragments of the VNAR-type immunoglobulin can be used.

Holt et al, "Domain antibodies:proteins for therapy" Trends in Biotechnology (2003):Vol. 21, No. 11:484-490, reviews antigen-binding fragments called "domain antibodies" or dAbs which comprise only the VH or VL domain of an antibody and are consequently smaller than, for example, Fab and scFv. DAbs are the smallest known antigen-binding fragments of antibodies, ranging from 11 kDa to 15 kDa. They are highly expressed in microbial cell culture. Each dAb contains three of the six naturally occurring complementarity determining regions (CDRs) from an antibody.

The immunoglobulin may be multivalent, i.e. bivalent, trivalent, tetravalent, in that it comprises more than one antigen binding site. The antigen binding sites may be derived from the same parent antibody or fragment thereof or from different antibodies which bind the same epitope. If all binding sites have the same specificity then a monospecific immunoglobulin is produced. Alternatively a multispecific immunoglobulin may be produced binding to different epitopes of the same antigen or even different antigens.

The immunoglobulin or fragment thereof of the VHH- or VNAR-type, or domain antibodies (dAbs) of the heavy or light chains of immunoglobulins or fragments thereof, may be naturally occurring i.e. elicited in vivo upon immunizing an animal with the desired antigen or synthetically made, i.e. obtained by genetic engineering techniques.

The antibody or fragment thereof may be naturally occurring or may be obtained by genetic engineering using techniques well known in the art.

The antibody can be chosen to be active against many different antigens, including micro-organisms, larger parasites, viruses and bacterial toxins.

Functional equivalents to VHH, VNAR and dAbs are also contemplated. A functional equivalent means a sequence which shows binding affinity for an antigen similar to the full length sequence. For example, additions or deletions of amino acids which do not result in a change of functionality are encompassed by the tern functional equivalents.

Techniques for synthesising genes, incorporating them into micro-organism hosts and expressing genes in micro-organisms are well known in the art and the skilled person would readily be able to put the invention into effect using common general knowledge. The use of replicating or integrating vectors is contemplated.

According to one embodiment of the present invention, a food product or pharmaceutical preparation comprises a delivery system for delivering antibodies to the GIT wherein the antibodies are heavy chain immunoglobulins or fragments thereof of the VHH- or VNAR-type, or domain antibodies (dAbs) of the heavy or light chains of immunoglobulins or fragments thereof, and they are active in the gut. Preferably, the delivery system is a micro-organism and the immunoglobulins are llama derived antibodies or fragments thereof. We have surprisingly found that these transformed micro-organisms will express llama heavy chain antibodies or fragments thereof on their surface and are able to reduce the viral load, normalize the pathology and mitigate the diarrhoea in an animal model of rotavirus infection. Furthermore, the llama heavy chain antibodies or fragments thereof were found to be very effective in reducing infection both in in vitro and in vivo models of rotavirus infection.

The use of fragments or portions of a whole antibody which can nevertheless exhibit antigen binding affinity is also contemplated. Fragments should preferably be functional fragments. A functional fragment of a heavy chain means a fragment of a heavy chain of an immunoglobulin which fragment shows binding affinity for an antigen similar to the full length sequence. Binding affinity is present when the dissociation constant is more than 10exp5. Such a fragment can be advantageously used in therapy, for example, as it is likely to be less immunogenic and, if needed, is more able to penetrate tissues due to its smaller size.

The antibodies are suitable for delivery to the GIT and must be able to be active in the stomach and/or gut. One advantage of the delivery system of the present invention includes that in vivo production or release of heavy chain immunoglobulin or fragments thereof of the VHH or VNAR type, or domain antibodies (dAbs) of the heavy or light chains of immunoglobulins or fragments thereof, locally in the GIT circumvents the practical problem of degradation of orally administered antibodies in the stomach.

In order to determine whether an immunoglobulin or fragments thereof of the VHH or VNAR type, or domain antibodies (dAbs) of the heavy or light chains of immunoglobulins or fragments thereof, will be suitable for use in the present invention the following test may be applied.

The antibody produced is selected under specific conditions of low pH, preferably from 1.5 to 3.5, and in the presence of pepsin (a protease abundant in the stomach) to result in highly beneficial molecules that work well in the GIT and are suitable for use according to the present invention.

The present application is applicable to the management of enteropathogenic micro-organisms in general. Preferably, the invention is directed to the management of enteropathogenic viruses and/or enteropathogenic bacteria. Management is understood to include therapy and/or prophylaxis.

Enteropathogenic bacteria may include, for example, *Salmonella, Campilobacter, E. coli* or *Helicobacter*. Enteropathogenic viruses may include, for example, Norovirus (Norwalk like virus), enteric adenovirus, Coronavirus, astroviruses, caliciviruses, and parvovirus. Rotavirus and the Norwalk family of viruses are the leading causes of viral gastroenteritis, however, a number of other viruses have been implicated in outbreaks. Most preferably, the present invention is directed the management of rotaviral infection.

The present application may also be used in the management of other non-enteropathogenic viruses like Hepatitis.

Alternatively, the delivery system may comprise a probiotic micro-organism. The probiotic micro-organism should preferably be able to survive passage in the GIT and should be active in the stomach/gut. Preferably, the micro-organism should be able to undergo transient colonization of the GIT; be able to express the gene in the GIT; and be able to stimulate the gut immune system.

Examples of suitable probiotic micro-organisms include yeast such as *Saccharomyces, Debaromyces, Kluyveromyces* and *Pichia*, moulds such as *Aspergillus, Rhizopus, Mucor* and *Penicillium* and bacteria such as the genera *Bifidobacterium, Propionibacterium, Streptococcus, Enterococcus, Lactococcus, Bacillus, Pediococcus, Micrococcus, Leuconostoc, Weissella, Oenococcus* and *Lactobacillus*.

Specific examples of suitable probiotic micro-organisms are:

*Kluyveromyces lactis, Kluyveromyces fragilis, Pichia pastoris, Saccharomyces cerevisiae, Saccharomyces boulardii, Aspergillus niger, Aspergillus oryzae, Mucor miehei, Bacillus subtilis, Bacillus natto, Bifidobacterium adolescentis, B. animalis, B. breve, B. bifidum, B. infantis, B. lactis, B. longum, Enterococcus faecium, Enterococcus faecalis, Escherichia coli, Lactobacillus acidophilus, L. brevis, L. casei, L. delbrueckii, L. fermentum, L. gasseri, L. helveticus, L. johnsonii, L. lactis, L. paracasei, L. plantarum, L. reuteri, L. rhamnosus, L. sakei, L. salivarius, Lactococcus lactis, Lactococcus cremoris, Leuconostoc mesenteroides, Leuconostoc lactis, Pediococcus acidilactici, P. cerevisiae, P. pentosaceus, Propionibacterium freudenreichii, Propionibacterium shermanii* and *Streptococcus salivarius*.

Particular probiotic strains are:

*Saccharomyces boulardii, Lactobacillus casei shirota, Lactobacillus casei immunitas, Lactobacillus casei* DN-114 001, *Lactobacillus rhamnosus* GG (ATCC53103), *Lactobacillus reuteri* ATCC55730/SD2112, *Lactobacillus rhamnosus* HN001, *Lactobacillus plantarum* 299v (DSM9843), *Lactobacillus johnsonii* La1 (I-1225 CNCM), *Lactobacillus plantarum* WCFS1, *Bifidobacterium lactis* HN019, *Bifidobacterium animalis* DN-173010, *Bifidobacterium animalis* Bb12, *Lactobacillus casei* 431, *Lactobacillus acidophilus* NCFM, *Lactobacillus reuteri* ING1, *Lactobacillus salivarius* UCC118, *Propionibacterium freudenreichii* JS, *Escherichia coli* Nissle 1917.

Conveniently, the micro-organism may be a lactic acid bacterium. More, preferably, the micro-organism is chosen from either the genus *Lactobacillus* or *Bifidobacterium*. Even more preferably, the micro-organism is *Lactobacillus*. Particularly, the *Lactobacillus* is *Lactobacillus casei* 393 pLZ15. *Lactobacillus casei* has recently been reidentified as *Lactobacillus paracasei* (Perez-Martinez, 2003).

The micro-organism may also be a probiotic *Bacillus* species, as described in Le H. Duc et al., Applied and Environmental Microbiology, 2004, p. 2161), and particularly preferred are *Bacillus cereus, Bacillus clausii* and *Bacillus pumilus*.

A system based on probiotic bacteria represents a safe and attractive approach and represents one of the cheapest antibodies production systems. The wide scale application of the micro-organism, preferably *Lactobacillus*, expressing antibodies is relatively easy and requires minimal handling and storage costs and economical.

Alternatively, the micro-organism may be a yeast. Suitable yeasts include the baker's yeast *S. cerevisiae*. Other yeasts like *Candida boidinii, Hansenula polymorpha, Pichia methanolica* and *Pichia pastoris* which are well known systems for the production of heterologous proteins and may be used in the present invention.

Filamentous fungi, in particular species from the genera *Trichoderma* and *Aspergillus* have the capacity to secrete large amounts of proteins, metabolites and organic acids into their culture medium. This property has been widely exploited by the food and beverage industries where compounds secreted by these filamentous fungal species have been used for decades.

It is understood that these micro-organisms may be genetically modified micro-organisms.

The delivery system according to this aspect will comprise a micro-organism transformed with the gene encoding the heavy chain immunoglobulin or fragment thereof of the VHH or VNAR type, or domain antibodies (dAbs) of the heavy or light chains of immunoglobulins or fragments thereof.

Such a system based on probiotic bacteria represents a safe and attractive approach to delivering antibodies to the GIT. Probiotic bacteria are well known in the art and represent one of the cheapest antibodies production systems. Hence, the wide scale application of the *lactobacilli* expressing antibodies is relatively easy and requires minimal handling and storage costs. Furthermore, the probiotic bacteria are able to colonize the gut at least temporarily, for days, weeks or months, will remain in the gut for longer and enable the constant production of the antibody to enable more constant and prolonged protection against an enteropathogenic micro-organism or virus.

The present invention is based on the findings that heavy chain immunoglobulins or fragments thereof of the VHH or VNAR type, or domain antibodies (dAbs) of the heavy or light chains of immunoglobulins or fragments thereof, of the invention may be used in the therapy or prophylaxis of infection by enteropathogenic micro-organisms.

More specifically, the immunoglobulins or fragments thereof of the VHH or VNAR type, or domain antibodies (dAbs) of the heavy or light chains of immunoglobulins or fragments thereof, may be used in the therapy or prophylaxis of viral gastroenteritis or diarrhoea caused by rotavirus.

A further advantage of the present invention is that the use of probiotic micro-organisms expressing immunoglobulins or functional fragments thereof of the VHH or VNAR type, or domain antibodies (dAbs) of the heavy or light chains of immunoglobulins or fragments thereof, enables the micro-organism, for example *Lactobacillus*, to provide the normal health benefits associated with this probiotic micro-organism, together with the prophylactic/therapeutic benefits in the management of the infection to be treated. This "dual effect" therapy provides synergistic effects and therefore greater health benefits to the subject than known in the art.

In accordance with one embodiment of the present invention, the heavy chain immunoglobulins or functional fragments thereof of the VHH type are derived from camelids, including llama and camels. An alternative source of heavy chain antibodies can be found in sharks. It recently has been shown that sharks also have a single VH-like domain in their antibodies termed VNAR. Fragments of VNAR-type immunoglobulin can be used in accordance with the present invention. Functional equivalents as described before are also contemplated. Alternatively, domain antibodies (dAbs) of the heavy or light chains of immunoglobulins or fragments thereof, may be used.

Preferably, the immunoglobulins are llama derived heavy chain antibodies or fragments thereof. Many llama derived heavy chain antibody fragments have been disclosed in the art. More preferred is the heavy chain immunoglobulin or fragment thereof which shows binding affinity with a dissociation constant of at least 10 exp 5 for rotavirus, especially rotavirus strains Wa, CK5, Wa1, RRV or CK5.

Llama heavy chain antibodies are particularly advantageous as they have surprisingly been found to be very effective in the treatment of rotaviral infection. Llama VHH antibody fragments have surprisingly been found to reduce the viral load, normalize the pathology and mitigate diarrhoea during rotavirus infection.

Particularly preferred LLama derived VHH sequences having affinity of rotavirus are provided by this specification in the sequence listing, SEQ ID No's 1 to 21. Alternatively, VHH sequences having at least 70%, 80%, 85%, 90%, 95%, 98% or 99% amino acid identity with SEQ ID No. 1 and having affinity for a rotavirus particle or antigen are also preferred embodiments according to this invention. VHH sequences may be derived from camellids, via immunization and/or by screening for affinity, but may also be derived from other mammalian species such as mice or humans and/or be camelized by amino acid substitutions, as described in the art. In another embodiment, the VHH sequences may be fused to yield multimeric units of 2, 3, 4, 5 or more VHH units, optionally linked via a spacer molecule. In another embodiment, several VHH sequences may be combined, separately or in one multimeric molecule. Preferably the VHH sequences have different specificities, for instance VHH sequences may be combined to provide a wide spectrum of affinities for a particular pathogen. In a highly preferred embodiment, 2, 3, 4, 5 or more VHH sequences having affinity for any one of rotavirus strains Wa, CK5, Wa1, RRV or CK5, may be combined, as separate monomeric units or as combined units on a carrier, for instance on a probiotic bacterium and/or on a multimeric molecule.

Furthermore, llama heavy chain antibodies have also unexpectedly been found to be suitable for administration in the GIT. Llama heavy chain antibodies were found to be highly resistant to protease degradation in the stomach and to withstand the acidic environment of the stomach. This is despite the fact that the proteolytic system in the GIT is more aggressive an environment than, for example encountered in the mouth. Activity in the gut is hampered by proteolytic activity, including protease and peptidase. We have now found that even more surprisingly the in vivo production or release of antibody fragments locally in the GIT circumvents the practical problem of degradation of orally administered antibodies in the stomach and gut. The present invention is the first system which enables expression of antibodies in the GIT which are suitable for the management of rotavirus infection.

When probiotic micro-organisms are chosen as the delivery system, we have found that these transformed micro-organisms will express llama heavy chain antibodies or fragments thereof on their surface and are able to reduce the viral load, normalize the pathology and mitigate the diarrhoea in an animal model of rotavirus infection.

The llama heavy chain antibodies are then expressed by the micro-organism in the GIT. Expression of the llama derived VHH antibody fragment may be both on the surface of the micro-organism and/or as a secreted protein of the micro-organism. Preferably secreted forms of the VHH antibody fragment is in multimeric form to enhance aggregation and clearance of the viral load.

Preferably, the micro-organism or more preferably a probiotic bacterium is transformed with an expression vector comprising the gene for the llama heavy chain antibody or fragments thereof. The expression vector may contain a constitutive promoter in order to express the antibodies or fragments thereof. Such a constitutive promoter will support in situ expression of antibodies by transformed *lactobacilli* persisting (at least for a short period) in the intestinal tract after administration. Alternatively, the promoter may be chosen to be active only in the GIT and/or stomach/gut i.e. suitable for GIT specific expression only. This will ensure expression and/or secretion of the llama heavy chain antibody or fragments thereof in the GIT, preferably the gut. Many constitutive promoters for *lactobacilli* are known in the art and an example of a promoter that is specifically inducible in the GIT is Pldh (Pouwels et al "*Lactobacilli* as vehicles for targeting antigens to mucosal tissues by surface exposition of foreign antigens" Methods in Enzymology (2001) 336:369-389).

The expression vectors described in the examples are able to replicate in the transformed *lactobacilli* and express the antibodies of fragments thereof. It will be understood that the present invention is not limited to these replication expression vectors only. The whole expression cassette can be inserted in a so-called "integration" plasmid, whereby the expression cassette will be integrated into the chromosome of the *lactobacilli* after transformation, as known in the art (Pouwels, P. H. and Chaillou, S. Gene expression in *lactobacilli* (2003) Genetics of lactic acid bacteria page 143-188).

According to an alternative embodiment, if encapsulation is chosen as the delivery system, the encapsulation method should survive passage to the stomach through the GIT and should be able to provide a sustained release of the antibody over a set period of time. This will ensure that the llama heavy chain antibody or fragment is delivered over time to the stomach. Llama heavy chain antibodies or VHH or VNAR fragments, or domain antibodies (dAbs) of the heavy or light chains of immunoglobulins or fragments thereof, are particularly suitable for this encapsulation method due to their ability to survive in the gut when released.

According to this embodiment of the present invention, delivery of the antibodies to the GIT can be effected by the use of encapsulates, such as those known in the food and pharmaceutical industries. Natural biopolymers may be used. Examples include Ca-alginate, carrageenan, gellan gum or gelatine. The delivery system may be an encapsulation method known in the art which will deliver the immunoglobulin or fragments thereof specifically to the gut. The encapsulate must therefore be able to survive until entry to the gut and then be released. Such a delivery system comprises a general protective system that protects the antibodies from degradation. Such techniques may include liposome entrapment, spinning disk and coacervation. Any trigger can be used to prompt the release of the encapsulated ingredient, such as pH change (enteric coating), mechanical stress, temperature, enzymatic activity. These techniques are expanded on in the article by Sebastien Gouin "Microencapsulation: industrial appraisal of existing technologies and trends" Food Science and Technology (2004) 15: 330-347. Preferably, an enteric coating is used. Additionally, the encapsulation method may allow the slow release of the antibody in the gut and/or stomach. This will enable a constant release of the antibody or functional fragment or equivalent over a set period of time.

The llama heavy chain antibodies or fragments thereof may be used in the therapy or prophylaxis of viral infection, such as viral gastroenteritis or rotavirus infection.

Specifically, the antibodies may be delivered to the GIT using a micro-organism transformed with llama heavy chain antibodies comprising the steps of i) transforming the micro-organism with the gene encoding llama heavy chain antibodies; and ii) administering the transformed micro-organism to the GIT of the human or animal in need of therapy.

The delivery system may comprise a micro-organism transformed with antibodies or fragments thereof the antibodies are expressed and/or secreted in the gut. Hence, use of a micro-organism as the delivery system has the advantages that in vivo production of antibody fragments locally in the GIT circumvents the practical problem of degradation of orally administered antibodies in the stomach. Such a system based on probiotic bacteria represents a safe and attractive approach to delivering antibodies to the GIT. Hence, the wide scale application of the *lactobacilli* expressing antibodies is relatively easy and requires minimal handling and storage costs and economical. Furthermore, the probiotic bacteria will remain in the gut for longer and enable the constant production of the antibody to enable more constant protection against the enteropathogenic microorganism.

Advantageously the amount of the micro-organism in food products of the invention is between $10^6$ and $10^{11}$ per serving or (for example if serving size is not known) between $10^6$ and $10^{11}$ per 100 g of product, more preferred these levels are from $10^8$ to $10^9$ per serving or per 100 g of product.

The antibodies for use according to the present invention must be active in the gut/stomach, i.e. they must be functional and retain their normal activity including inactivating their target. The active antibodies according to the invention should bind to their target as normal, thus, the binding affinity of the antibody for the antigen should be as normal. Binding affinity is present when the dissociation constant is more than $10^5$.

Hence, the food product or pharmaceutical preparation according to the invention will be able to selectively address a specific disease or symptom of a disease. The choice of antibody will determine the disease or symptom to be treated or reduced.

It will be understood that when the product is a food product any antibody may be used. However, when the product is a pharmaceutical preparation heavy chain immunoglobulins or fragments thereof of the VHH or VNAR type or domain antibodies (dabs) of the heavy or light chains of immunoglobulins or fragments thereof are preferred.

Preferably, the antibody or fragments thereof should have one or more of the following characteristics:
 i) They show good binding affinity and the desired inhibition functionality under the conditions present in the G/I tract; and
 ii) They have good proteolytic stability in that they are stable against degradation by proteolytic enzymes.
 iii) The antibodies should be thermostable which enables their inclusion in a variety of food products. The food products may be prepared in a process requiring pasteurization and it is preferred that the activity of the antibodies is largely maintained despite heat treatment.

The antibody or fragment thereof should be able to be expressed and secreted in the gut. Several assays are well known in the art which mimic GIT conditions and are used for instance to select suitable probiotics that can survive GIT conditions. A suitable assay for determining whether an antibody can survive the GIT conditions is described by Picot, A. and Lacroix, C. (International Dairy Journal 14 (2004) 505-515).

In order to determine whether an antibody will be suitable for use in the present invention the following test may be applied. The antibody produced is selected under specific conditions of low pH, preferably from 1.5 to 3.5, and in the presence of pepsin (a protease abundant in the stomach) to result in highly beneficial molecules that work well in the G/I tract and are suitable for use according to the present invention.

The present application may be applicable to the management of enteropathogenic micro-organisms in general. Enteropathogenic micro-organisms include viruses or enteropathogenic bacteria. Management is understood to mean therapy and/or prophylaxis.

One further embodiment of the invention is a food product or pharmaceutical preparation containing the delivery system described above. Several food products may be prepared according to the invention, for example meal replacers, soups, noodles, ice-cream, sauces, dressing, spreads, snacks, cereals, beverages, bread, biscuits, other bakery products, sweets, bars, chocolate, chewing gum, diary products, dietetic products e.g. slimming products or meal replacers etc. For some applications food products of the invention may also be dietary supplements, although the application in food products of the above type is preferred.

Table 1 indicates a number of products, which may be prepared according to the invention, and a typical serving size.

TABLE 1

| Product | Serving Size |
|---|---|
| margarine | 15 g |
| ice-cream | 150 g |
| dressing | 30 g |
| sweet | 10 g |
| bar | 75 g |
| meal replacer drink | 330 ml |
| beverages | 200 ml |

An alternative means of administration of the delivery system comprising a micro-organism transformed with antibodies or functional fragments thereof comprises a dispensing implement for administering food which contains a coating of the delivery system on at least one of its surfaces. The term dispensing implement covers tube, straws, spoons or sticks or other implements which are used to deliver a liquid or semi-solid food product to a consumer. The dispensing implement may also be used to deliver a solid food product to a consumer. This dispensing tube or straw is especially suitable for use with certain beverages where high or low pH and/or temperature means that direct addition of the micro-organism to the beverage is not recommended The dispensing implement can also be used when the delivery system of the invention comprises encapsulated antibodies or even with antibodies per se.

The dispensing implement contains on at least one surface a coating of the micro-organism, encapsulated antibodies or antibodies per se After the dispensing implement is coated with these particles, the implement is stored in an outer envelope which is impermeable to moisture and other contamination. The coating material which contains these particles is non-toxic to humans and to bacteria and can be an oil such as corn oil or a wax. This aspect is described in U.S. Pat. No. 6,283,294 B1. Once the dispensing implement containing these particles penetrates the beverage or semi-solid food product, the particles are integrated into the food product, giving a desirable dose of the antibodies with a serving of the product.

Preferably, the encapsulated particle, antibody per se or the micro-organism may be suspended in water which is then applied to the dispensing implement and evaporated. By using this method the dispensing implement will have a coating of the encapsulated particle, antibody per se or the micro-organism, which can then be released when the dispensing implement comes into contact with the liquid or semi-solid food product.

A still further embodiment of the invention relates to a method for making a food product or pharmaceutical preparation comprising a delivery system for delivering antibodies to the GIT wherein the antibodies are active in the gut comprising adding the delivery system to the food product or pharmaceutical preparation during the manufacture of the food product.

It is essential that the micro-organism is alive in the product, thus, for example, if the product is heated during processing, the micro-organism has to be added after the heating step (post-dosing). However, if a product is fermented with the micro-organism, a heating step after the fermentation will not be acceptable. If the product is a liquid product, administration of the micro-organism could take place by use of a dispensing implement such as a drinking straw.

A further embodiment of the invention relates to the use of the food product or pharmaceutical preparation comprising the delivery system according to the invention to deliver health benefits to the gut of a subject after administration. Such health benefits include the specific health benefit the antibody may provide. The micro-organism itself may also provide several health effects for example relating to gut well being such as IBS (Irritable Bowel Syndrome), reduction of lactose maldigestion, clinical symptoms of diarrhoea, immune modulation, anti-tumor activity, adjuvant effects and enhancement of mineral uptake.

The food product or pharmaceutical preparation according to the present invention may be suitable for the management, including treatment or prophylaxis of infections caused by enteropathogenic bacteria or viruses. Other antibodies which may be incorporated into the invention will be able to provide a multitude of other health benefits.

The present invention is based on the finding that heavy chain immunoglobulins or fragments thereof of the VHH- or VNAR-type, or domain antibodies (dAbs) of the heavy or light chains of immunoglobulins or fragments thereof, of the invention may be used in the therapy or prophylaxis of infection by enteropathogenic micro-organisms. Furthermore, the immunoglobulins or fragments thereof of the VHH- or VNAR-type, or domain antibodies (dAbs) of the heavy or light chains of immunoglobulins or fragments thereof, may be used in the therapy or prophylaxis of viral gastroenteritis or diarrhoea caused by the enteropathogenic microorganism rotavirus.

A further advantage of the present invention is that the use of food products or pharmaceutical preparations comprising probiotic micro-organisms expressing immunoglobulins or fragments thereof of the VHH- or VNAR-type, or domain antibodies (dAbs) of the heavy or light chains of immunoglobulins or fragments thereof, enables the micro-organism, for example *Lactobacillus*, to provide the normal health benefits associated with this probiotic micro-organism, together with the prophylactic/therapeutic benefits in the management of the infection to be treated. This "dual effect" therapy provides greater health benefits to the subject than that known in the art.

In accordance with another embodiment of the present invention, the heavy chain immunoglobulins or fragments thereof of the VHH type are derived from camelids, including llama and camels. Many llama derived heavy chain antibody fragments have been disclosed in the art. More preferred is the heavy chain immunoglobulin or fragment thereof which shows binding affinity with a dissociation constant of at least 10 exp 5 for rotavirus, especially rotavirus strains Wa, CK5, Wa1, RRV or CK5.

We have surprisingly found that llama heavy chain antibodies are effective in the management of rotavirus infection. When the antibodies used are llama heavy chain antibodies, the health benefit delivered will include an anti-diarhoeal effect. Hence, llama heavy chain antibodies can be used in the management of rotavirus infection, including the therapy or prophylaxis of rotavirus infection. We have found that llama VHH antibody fragments can reduce the viral load, normalize the pathology and mitigate diarrhoea during rotavirus infection. Rotavirus continues to be the single most common cause of infantile diarrhoea in the world and most children get infected during the first 5 years of life. In developing countries, rotavirus induced diarrhoea may cause 600,000 to 870,000 deaths each year and in developed countries, rotavirus disease accounts for immense economic loss.

Furthermore, llama heavy chain antibodies have also unexpectedly been found to be suitable for administration in the gut. We have surprisingly found that the llama heavy chain antibodies were found to be highly resistant to protease degradation in the stomach and to withstand the acidic environment of the stomach. This is despite the fact that the proteolytic system in the gut/stomach is more aggressive an environment than, for example encountered in the mouth. The in vivo production of antibody fragments locally in the GIT circumvents the practical problem of degradation of orally administered antibodies in the stomach. The present invention is the first system which enables expression of antibodies in the GIT which are suitable for the management of rotavirus infection.

Hence, the use of food products or pharmaceutical preparations comprising *lactobacilli* expressing llama heavy chain antibodies enables the *lactobacilli* to provide the normal health benefits associated with this probiotic together with the prophylactic/therapeutic benefits in the management of rotavirus infection. The present invention is the first system which enables expression of antibodies in the GIT which are suitable for the management of rotavirus infection.

It will be understood that the food product or pharmaceutical preparation can be administered in order to deliver a health benefit to the subject and/or to combat a specific disease or infection. The choice of the antibody will depend on the disease to be treated.

Preferably, the micro-organism is transformed with an expression vector comprising the gene for the llama heavy chain antibody or fragment thereof. Either an integrating or a replicating vector may be used.

If encapsulation is chosen as the delivery system, the encapsulation method should survive passage to the stomach through the GIT and should be able to provide a sustained release of the antibody over a set period of time. This will ensure that the llama heavy chain antibody or fragment is delivered over time to the stomach. Llama heavy chain antibodies or heavy chains thereof are particularly suitable for this encapsulation method due to their ability to survive in the gut when released.

Specifically, the antibodies may be delivered to the GIT using a micro-organism transformed with llama heavy chain antibodies comprising the steps of i) transforming the micro-organism with the gene encoding llama heavy chain antibodies; and ii) administering the transformed micro-organism to the GIT of the human or animal in need of therapy.

Margarines and Other Spreads

Typically these are oil in water or water in oil emulsions, also spreads which are substantially fat free are covered. Typically these products are spreadable and not pourable at the temperature of use e.g. 2-10° C. Fat levels may vary in a wide range e.g. full fat margarines with 60-90 wt % of fat, medium fat margarines with 30-60 wt % of fat, low fat products with 10-30 wt % of fat and very low or fat free margarines with 0 to 10 wt % of fat.

The fat in the margarine or other spread may be any edible fat, often use are soybean oil, rapeseed oil, sunflower oil and palm oil. Fats may be used as such or in modified form e.g. hydrogenated, esterified, refined etc. Other suitable oils are well known in the art and may be selected as desired.

The pH of a margarine or spread may advantageously be from 4.5 to 6.5.

Examples of spreads other than margarines are cheese spreads, sweet spreads, yogurt spreads etc.

Optional further ingredients of spreads may be emulsifiers, colourants, vitamins, preservatives, gums, thickeners etc. The balance of the product will normally be water.

A typical size for an average serving of margarine or other spreads is 15 grams. Preferred VHH-producing *Lactobacillus* in the margarine or spread are $10^6$ and $10^{11}$ per serving most preferred $10^8$ to $10^{10}$ per serving. The *Lactobacillus* strain has to be added aseptically after the heating steps in the process. Alternatively, encapsulated VHH's may be added to these food products. Preferably between 25 and 5000 µg per serving is added, more preferably between 50 and 500 µg are added per serving. Most preferably two or three servings are given each day.

Frozen Confectionary Products

For the purpose of the invention the term frozen confectionery product includes milk containing frozen confections such as ice-cream, frozen yoghurt, sherbet, sorbet, ice milk and frozen custard, water-ices, granitas and frozen fruit purees.

Preferably the level of solids in the frozen confection (e.g. sugar, fat, flavouring etc) is more than 3 wt %, more preferred from 10 to 70 wt %, for example 40 to 70 wt %.

Ice-cream will typically comprise 2 to 20 wt % of fat, 0 to 20 wt % of sweeteners, 2 to 20 wt % of non-fat milk components and optional components such as emulsifiers, stabilisers, preservatives, flavouring ingredients, vitamins, minerals, etc, the balance being water. Typically ice-cream will be aerated e.g. to an overrun of 20 to 400%, more general 40 to 200% and frozen to a temperature of from −2 to −200° C., more general −10 to −30° C. Ice-cream normally comprises calcium at a level of about 0.1 wt %.

A typical size of an average serving of frozen confectionary material is 150 grams. Preferred *Lactobacillus* levels are from $10^6$ and $10^{11}$ per serving, more preferred these levels are from $10^7$ to $10^{10}$ per serving most preferred $10^8$ to $10^9$ per serving. The *Lactobacillus* strain has to be added aseptically after the heating steps in the process. Alternatively, encapsulated VHH's may be added to these food products. Preferably between 25 and 5000 µg per serving is added, more preferably between 50 and 500 µg are added per serving. Most preferably two or three servings are given each day.

Beverages, for Example Tea Based Products or Meal Replacers

*Lactobacillus* can advantageously be used to beverages for example fruit juice, soft drinks etc. A very advantageous beverage in accordance to the invention is a tea based product or a meal replacers drink. These products will be described in more detail herein below. It will be apparent that similar levels and compositions apply to other beverages comprising vitamin producing *Lactobacillus* bacteria.

For the purpose of this invention the term tea based products refers to products containing tea or tea replacing herbal compositions e.g. tea-bags, leaf tea, herbal tea bags, herbal infusions, powdered tea, powdered herbal tea, ice-tea, ice herbal tea, carbonated ice tea, carbonated herbal infusion etc.

Typically some tea based products of the invention may need a preparation step shortly before consuming, e.g. the making of tea brew from tea-bags, leaf tea, herbal tea bags or herbal infusions or the solubilisation of powdered tea or powdered herbal tea. For these products it is preferred to adjust the level of *Lactobacillus* in the product such that one serving of the final product to be consumed has the desired levels of *Lactobacillus* as described above.

For ice-tea, ice herbal tea, carbonated ice tea, carbonated herbal infusions the typical size of one serving will be 200 ml or 200 grams.

Meal replacer drinks are typically based on a liquid base which may for example be thickened by means of gums or fibres and whereto a cocktail of minerals and vitamins are added. The drink can be flavoured to the desired taste e.g. fruit or choco flavour. A typical serving size may be 330 ml or 330 grams.

Both for tea based beverages and for meal replacer drinks, preferred *Lactobacillus* levels are $10^6$ and $10^{11}$ per serving, more preferred these levels are form $10^7$ to $10^{10}$ per serving most preferred $10^8$ to $10^9$ per serving. Alternatively, encapsulated VHH's may be added to these food products. Preferably between 25 and 5000 µg per serving is added, more preferably between 50 and 500 µg are added per serving. Most preferably two or three servings are given each day.

For products which are extracted to obtain the final product, generally the aim is to ensure that one serving of 200 ml or 200 grams comprises the desired amounts as indicated above. In this context, it should be appreciated that normally only part of the *Lactobacillus* present in the tea based product to be extracted will eventually be extracted into the final tea drink. To compensate for this effect generally it is desirable to incorporate into the products to be extracted about 2 times the amount as is desired to have in the extract.

For leaf tea or tea-bags typically 1-5 grams of tea would be used to prepare a single serving of 200 mls.

If tea-bags are used, the *Lactobacillus* may advantageously be incorporated into the tea component. However it will be appreciated that for some application it may be advantageous to separate the *Lactobacillus* from the tea, for example by incorporating it into a separate compartment of the tea bag or applying it onto the tea-bag paper.

Salad Dressings or Mayonnaise

Generally dressings or mayonnaise are oil in water emulsions, the oil phase of the emulsion generally is 0 to 80 wt % of the product. For non fat reduced products the level of fat is typically from 60 to 80%, for salad dressings the level of fat is generally 10-60 wt %, more preferred 15-40 wt %, low or no fat dressings may for example contain triglyceride levels of 0, 5, 10, 15% by weight.

Dressings and mayonnaise are generally low pH products having a preferred pH of from 2-6.

Dressings or mayonnaise optionally may contain other ingredients such as emulsifiers (for example egg-yolk), stabilisers, acidifiers, biopolymers, bulking agents, flavours, colouring agents etc. The balance of the composition is water which could advantageously be present at a level of 0.1 to 99.9 wt %, more general 20-99 wt %, most preferred 50 to 98 wt %.

A typical size for an average serving of dressings or mayonnaise is 30 grams. Preferred levels of *Lactobacillus* in such products would be $10^6$ and $10^{11}$ per serving, more preferred these levels are from $10^7$ to $10^{10}$ per serving most preferred $10^8$ to $10^9$ per serving. The *Lactobacillus* strain has to be added aseptically after the heating steps in the process. Alternatively, encapsulated VHH's may be added to these food products. Preferably between 25 and 5000 µg per serving is added, more preferably between 50 and 500 µg are added per serving. Most preferably two or three servings are given each day.

Meal Replacer Snacks or Bars

These products often comprise a matrix of edible material wherein the Lactobacillus can be incorporated. For example the matrix may be a fat based (e.g. couverture or chocolate) or may be based on bakery products (bread, dough, cookies etc) or may be based on agglomerated particles (rice, grain, nuts, raisins, fruit particles).

A typical size for a snack or meal replacement bar could be 20 to 200 g, generally from 40 to 100 g. Preferred levels of Lactobacillus in such products would be $10^6$ and $10^{11}$ per serving, more preferred these levels are from $10^7$ to $10^{10}$ per serving most preferred $10^8$ to $10^{10}$ per serving. The Lactobacillus strain has to be added aseptically after the heating steps in the process. Alternatively, encapsulated VHH's may be added to these food products. Preferably between 25 and 5000 µg per serving is added, more preferably between 50 and 500 µg are added per serving. Most preferably two or three servings are given each day.

Further ingredients may be added to the product such as flavouring materials, vitamins, minerals etc.

For each of the above food products, the amount of Lactobacillus per serving has been given as a preferred example. It will be understood that alternatively any suitable probiotic micro-organism may be present at this level.

Lemonade Powder

Lactobacillus can also be used in dry powders in sachets, to be dissolved instantly in water to give a refreshing lemonade. Such a powder may have a food-based carrier, such as maltodextrin or any other. Optional further ingredients may be colourants, vitamins, minerals, preservatives, gums, thickeners etc.

A typical size for an average serving or margarine or other spreads is 30-50 grams. Preferred VHH-producing Lactobacillus in the lemonade powder are $10^6$ and $10^{11}$ per serving most preferred $10^8$ to $10^{10}$ per serving. The Lactobacillus strain has to be sprayed on the carrier in such a way that it is kept alive, according to methods known by those skilled in the art. Alternatively, encapsulated VHH's may be added to these food products. Preferably between 25 and 5000 µg per serving is added, more preferably between 50 and 500 µg are added per serving.

In all the above products the transformed micro-organism can be added as viable cultured (wet) biomass or as a dried preparation, still containing the viable micro-organisms as known in the art.

The present invention is now further illustrated by way of the following examples.

EXAMPLES

Examples 1 to 3: Generation of Antibody fragments with subsequent in-vitro and in-vivo testing.

Example 1

Selection of Rotavirus Specific Heavy-Chain Antibody Fragments from a Llama Immune Phage Display Library and Production in Yeast.

Rhesus rotavirus strain RRV (serotype G3) was purified, amplified and concentrated as described previously (Svensson L., Finlay B. B., Bass D., Vonbonsdorff C. H., Greenberg H. B. "Symmetrical infection on polarised human intestinal epithelial (CaCo-2) cells". J Virol. (1991) 65, 4190-4197.

A llama was immunized subcutaneously and intramuscularly at day 0, 42, 63, 97 and 153 with $5 \times 10^{12}$ pfu of rotavirus strain RRV.

Prior to immunization, the viral particles were taken up in oil emulsion (1:9 V/V, antigen in PBS: Specol (Bokhout, B. A., Van Gaalen, C., and Van Der Heijden, Ph. J. "A selected water-in-oil emulsion: composition and usefulness as an immunological adjuvant". Vet. Immunol. Immunopath. (1981) 2: 491-500 and Bokhout, B. A., Bianchi, A. T. J., Van Der Heijden, Ph. J., Scholten, J. W. and Stok, W. "The influence of a water-in-oil emulsion on humoral immunity". Comp. Immun. Microbiol. Infect. Dis. (1986) 9: 161-168. as described before (Frenken, L. G. J., et al. "Isolation of antigen specific Llama VHH antibody fragments and their high level secretion by Saccharomyces cerevisiae". J. Biotechnol. (2000) 78, 11-21). The immune response was followed by titration of serum samples in ELISA with RRV rotavirus coated at a titer of $4 \times 10^6$ pfu/ml in 0.9% NaCl following the protocol described before (De Haard, H. J., van Neer, N., Reurs, A., Hufton, S. E., Roovers, R. C., Henderikx P., de Bruine A. P., Arends J. W., and Hoogenboom, H. R. "A large non-immunized human Fab fragment phage library that permits rapid isolation and kinetic analysis of high affinity antibodies". J. Biol. Chem. (1999) 274: 18218-18230; Frenken, L. G. J., et al. "Isolation of antigen specific Llama VHH antibody fragments and their high level secretion by Saccharomyces cerevisiae". J. Biotechnol. (2000) 78, 11-21).

An enriched lymphocyte population was obtained from the 153-day blood sample of about 150 ml via centrifugation on a Ficoll (Pharmacia) discontinuous gradient. From these cells, total RNA (between 250 and 400 ug) was isolated by acid guanidium thiocyanate extraction Chomczynski, P. and Sacchi, N. "Single-step method of RNA isolation by acid guanidinium thiocyanate-phenol-chloroform extraction". Anal. Biochem. (1987)162:156-159. Subsequently, first strand cDNA was synthesized using the Amersham first strand cDNA kit (RPN1266). In a 20 µl reaction mix 0.4-1 µg mRNA was used. The 6-mer random primer was used to prime the first DNA strand. After cDNA synthesis, the reaction mix was directly used for amplification by PCR. VHH genes were amplified with primers Lam-16: (GAGGTBCARCTGCAGGASAGYGG) (SEQ ID NO: 22);

Lam-17: (GAGGTBCARCTGCAGGASTCYGG) (SEQ ID NO: 23);

Lam-07 (priming to the short hinge regions; and

Lam-08 (long hinge specific).

(Frenken, L. G. J., et al. "Isolation of antigen specific Llama VHH antibody fragments and their high level secretion by Saccharomyces cerevisiae". J. Biotechnol. (2000) 78, 11-21). Amplification of DNA was performed as described by De Haard, H. J., van Neer, N., Reurs, A., Hufton, S. E., Roovers, R. C., Henderikx P., de Bruine A. P., Arends J. W. and Hoogenboom H. R. "A large non-immunized human Fab fragment phage library that permits rapid isolation and kinetic analysis of high affinity antibodies". J. Biol. Chem. (1999) 274: 18218-18230.

The amplified products were digested with PstI and NotI (New England Biolabs, US) and cloned in phagemid vector pUR5071, which is based on pHEN1 (Hoogenboom, H. R., Griffiths, A. D., Johnson, K. S., Chiswell, D. J., Hudson, P. and Winter, G. "Multi-subunit proteins on the surface of filamentous phage: methodologies for displaying antibody (Fab) heavy and light chains". Nucleic Acids Res. (1991) 19: 4133-4137) and contains a hexahistidine tail for Immobilized Affinity Chromatography (Hochuli, E., Bannwarth, W., Döbeli, H., Gentz, R. and Stüber, D. "Genetic approach to facilitate purification of recombinant proteins with a novel metal chelate adsorbent". Bio/Technol. (1988) 6:1321-1325) and a c-myc derived tag (Munro S. and Pelham H. R. "An Hsp70-like protein in the ER: identity with the 78 kd glucose-regulated protein and immunoglobulin heavy chain binding protein". Cell (1986) 46: 291-300) for detection. Ligation and transformation were performed as was described before (De Haard, H. J., van Neer, N., Reurs, A., Hufton, S. E., Roovers, R. C., Henderikx P., de Bruine A. P., Arends J. W. and Hoogenboom H. R. "A large non-immunized human Fab fragment phage library that permits rapid isolation and kinetic analysis of high affinity antibodies". J. Biol. Chem. (1999) 274: 18218-18230). The rescue with helperphage VCS-M13 and PEG precipitation was performed as described by Marks, J. D., Hoogenboom, H. R., Bonnert, T. P., McCafferty, J., Griffiths, A. D. and Winter, G. "By-passing immunization: Human antibodies from V-gene libraries displayed on phage". J. Mol. Biol. (1991) 222: 581-597.

Selections of rotavirus specific phages were performed via the biopanning method (Marks J. D., Hoogenboom, H. R., Bonnert, T. P., McCafferty, J., Griffiths, A. D. and Winter, G. "By-passing immunization: Human antibodies from V-gene libraries displayed on phage". J. Mol. Biol. (1991) 222: 581-597) by coating of rotavirus strain RRV ($2.5 \times 10^7$ pfu/ml at round 1; $5 \times 10^4$ pfu/ml at round 2; 500 pfu/ml at round 3). Immunotubes (Nunc, Roskilde, Denmark) were coated overnight at 4° C. with either a 1:1000 dilution of anti-rotavirus rabbit sera or anti-rotavirus guinea pig sera in carbonate buffer (16% (v/v) 0.2 M NaHCO3+9% (v/v) 0.2 M Na2CO3). Viral particles were captured via polyclonal anti-rotavirus sera. In addition to the standard selections, the antibody fragment displaying phages have selected in an acidic environment. This was done by selecting in a dilute HCl solution (pH 2.3). After this adapted selection process, the standard procedure was followed.

Soluble VHH was produced by individual E. coli TG1 clones as described by Marks J. D., Hoogenboom, H. R., Bonnert, T. P., McCafferty, J., Griffiths, A. D. and Winter, G. "By-passing immunization: Human antibodies from V-gene libraries displayed on phage". J. Mol. Biol. (1991) 222: 581-597. Culture supernatants were tested in ELISA. Microlon F (Greiner Bio-One GmbH, Germany) plates were coated with 50 µl/well of a 1:1000 dilution of either anti-rotavirus rabbit polyclonal sera or anti-rotavirus guinea pig polyclonal sera in carbonate buffer (16% (v/v) 0.2 M NaHCO3+9% (v/v) 0.2 M Na2CO3) and subsequently incubated with rotavirus strain RRV or CK5 (approx. 109 pfu/ml). After incubation of the VHH containing supernatants, VHH's were detected with a mixture of the mouse anti-myc monoclonal antibody 9E10 (500 ng/ml, in-house production) and anti-mouse HRP conjugate (250 ng/ml, Dako, Denmark). Alternatively, detection was performed with anti-6×His-HRP antibody conjugate (1000 ng/ml, Roche Molecular, US). Fingerprint analysis (Marks, J. D., Hoogenboom, H. R., Bonnert, T. P., McCafferty, J., Griffiths, A. D. and Winter, G. "By-passing immunization: Human antibodies from V-gene libraries displayed on phage". J. Mol. Biol. (1991) 222: 581-597) with the restriction enzyme HinFI (New England Biolabs, US) was performed on all clones. Sequencing was performed at Baseclear B. V. (Leiden, The Netherlands).

A set of rotavirus-specific antibody fragments was selected. DNA sequences encoding these antibody fragments were isolated from pUR5071 (PstI/BstEII, New England Biolabs, US)) and cloned into pUR4547 which is identical to the previously described pUR4548 (Frenken, L. G. J., et al. "Isolation of antigen specific Llama VHH antibody fragments and their high level secretion by *Saccharomyces cerevisiae*". J. Biotechnol. (2000) 78, 11-21) but does not encode any C-terminal tag-sequences. This episomal yeast expression vector contains the GAL7 promoter, the SUC2 signal sequence for high level expression and secretion into the growth medium, respectively. The *S. cerevisiae* strain VWK18gal1 was transformed and induced for antibody fragment production as described previously (Van der Vaart, J. M., "Expression of VHH antibody fragments in *Saccharomyces cerevisiae*". In Methods in Molecular Biology (2001) Vol. 178, p 359-366, Edited by P. M. O'Brien and R. Aiken, Humana Press Inc., Totowa, N.J.). Antibody fragments were purified and concentrated by filtration over microcon filters with a 10 kDa cut-off (Amicon, US).

Results:

Total overview of anti Rotavirus VHH fragments are listed in the table below, sequences of the VHH fragments are provided in the sequence listing and FIG. 12.

| Ligand | Original E. coli clone | Yeast clone Episomal Production | SEQ ID No.: | Neutralization |
|---|---|---|---|---|
| Anti-rota VHH1 | 2B10 | +++ | 1 | +++ (in vivo) |
| Anti-rota VHH2 | 1D3 | ++ | 2 | ++ (in vivo) |
| Anti-rota VHH3 | 1F6 | ++ | 3 | ++ (in vivo) |
| Anti-rota VHH4 | 1H4 | ++ | 4 | ++ (in vitro) |
| Anti-rota VHH5 | GP-P3A-6E | +++ | 5 | — |
| Anti-rota VHH6 | 1B5 | +++ | 6 | — |
| Anti-rota VHH7 | RAB-P3A-6C | + | 7 | — |
| Anti-rota VHH8 | 1B2 | ++ | 8 | — |
| Anti-rota VHH9 | 2A12 | + | 9 | — |
| Anti-rota VHH10 | RAB-P1-2G | + | 10 | + (in vivo) |
| Anti-rota VHH11 | 1G6 | +++ | 11 | +/− (in vitro) |
| Anti-rota VHH12 | 2E4 | +++ | 12 | ++ (in vivo) |
| Anti-rota VHH13 | 2F11 | ++ | 13 | — |
| Anti-rota VHH14 | RAB-P1-1F | +++ | 14 | ++ (in vivo) |
| Anti-rota VHH15 | 1B8 | + | 15 | +/− (in vitro) |
| Anti-rota VHH16 | 3E7 | +++ | 16 | — |
| Anti-rota VHH17 | 1D2 | ++ | 17 | +++ (in vitro) |
| Anti-rota VHH18 | 1E4 | +++ | 18 | + (in vitro) |
| Anti-rota VHH19 | 1D4 | +/− | 19 | ++ (in vitro) |
| Anti-rota VHH20 | 1A1 | + | 20 | ++ (in vitro) |
| Anti-rota VHH21 | 1E1 | ++++ | 21 | — |

Example 2

In Vitro Inhibition of Rotavirus

Bovine Rotavirus Compton CK5 was obtained from the Moredun Institute, Midlothian, Scotland and the BS-C1 cells were purchased from the European Animal Cell Culture Collection.

The BS-C1 cells were cultured in Earles Modified Essential Medium supplemented with 10% Heat inactivated foetal calf serum, 1% MEM Amino Acids solution (100×), 20 mmol 1-1 L-Glutamine, 100 I.U. ml-1 penicillin, 100 µg ml-1 streptomycin and 2.5 µg ml-1 amphotericin B (all from Sigma, US).

CK5 Rotavirus stock was diluted in Serum Free Medium (SFM) EMEM supplemented with 1% MEM Amino Acids solution (100×), 20 mmol 1-1 L-Glutamine and 0.5 µg/ml crystalline trypsin and then 5 ml of diluted seed was added to confluent monolayers of BS-C1 cells in 162 cm² tissue culture flasks (Costar, UK). The virus was adsorbed onto the cells for one hour at 37° C. then the medium was topped up to 75 ml. The bottles were incubated at 37° C. until complete cytopathic effect was observed. Cultures were frozen (−70°

C.) and thawed twice, then pooled and centrifuged at 1450 g for 15 minutes at 4° C. to remove cell debris. The supernatant was decanted and stored in aliquots at −70° C.

Monolayers of BS-C1 cells were cultured in 12-well tissue culture plates at 37° C. in an atmosphere of 95% air and 5% carbon dioxide. The medium was removed and replaced with SFM for at least 2 hours prior to use. The CK5 virus was diluted to give approximately 50 pfu/ml in SFM. The selected anti-rotavirus fragments were diluted in SFM and then equal volumes of virus and fragment dilution were mixed (200 µl total volume) and incubated for one hour at 37° C.

The virus-fragment mixtures were then plated onto the monolayers of cells (three replicate wells each). The plates were incubated for one hour at 37° C. in an atmosphere of 95% air and 5% carbon dioxide. Subsequently, the virus was removed and an overlay consisting of 0.75% Sea Plaque Agarose (FMC) in EMEM containing 100 I.U. ml-1 penicillin, 100 µg ml-1 streptomycin, 2.5 µg ml-1 amphotericin B and 0.1 µg/ml crystalline trypsin was added. Plates were then incubated at 37° C. in an atmosphere of 95% air and 5% carbon dioxide for 4 days. After fixing and staining with 1% crystal violet in 10% formaldehyde, the agarose was removed, the wells washed with water and the plaques counted.

From 23 clones tested according to the method describe above, nine produced antibody fragments capable of neutralising this rotavirus strain. Fragments 2B10 and 1D3 most effectively neutralised rotavirus in the plaque assays (FIG. 1)

Figure 1A:
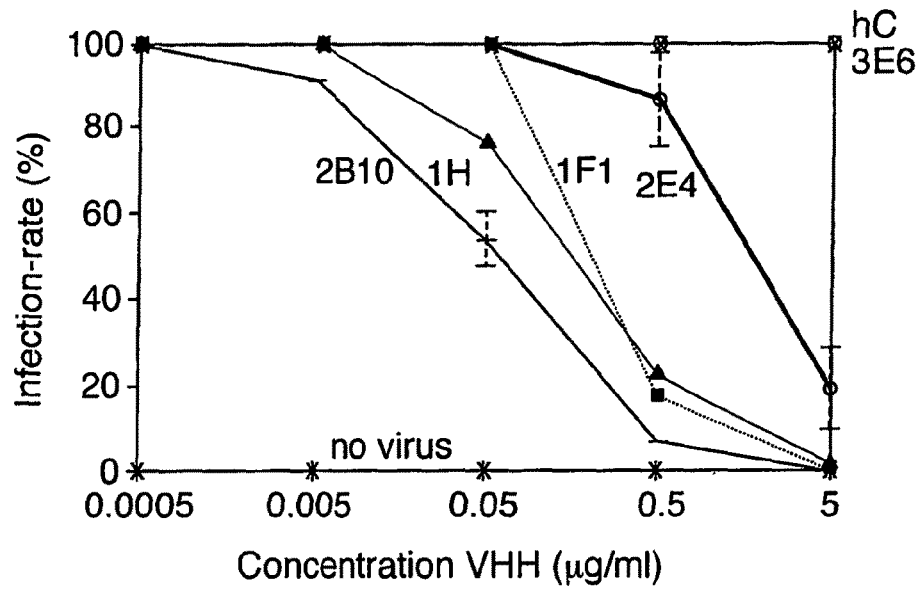
FIGS. 1a and b shows that rotavirus specific VHH particles neutralise rotavirus in-vitro.
Figure 1B:
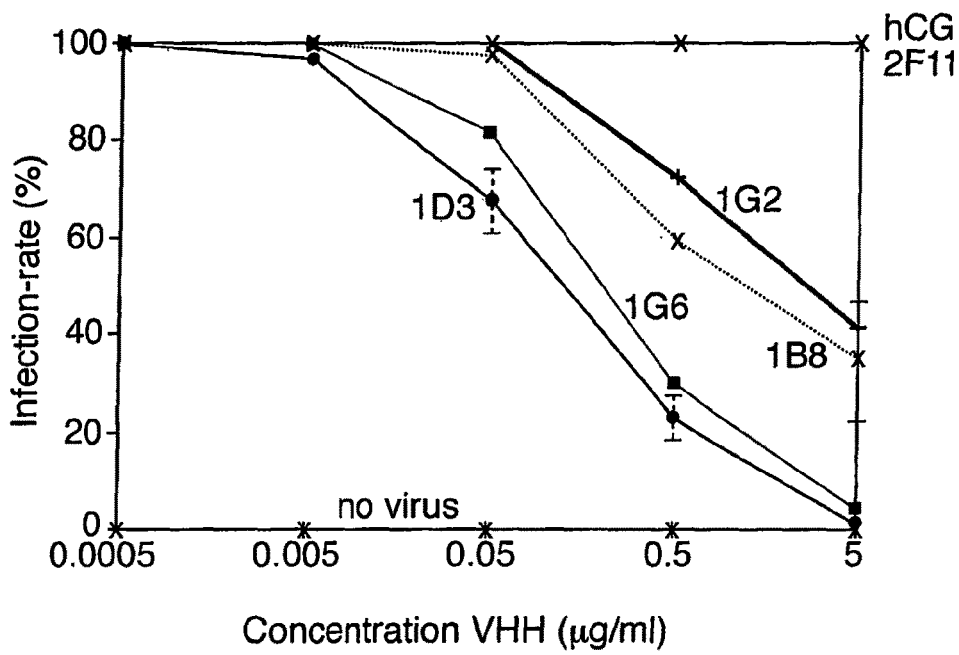

FIG. 1 shows virus neutralisation of rotavirus CK5 determined by an in vitro plaque assay. The average neutralisation-rate from the four obtained measurements is indicated at each data-point. If there is a spread of over 10% at a data point, the two most extreme measurements are indicated (dashed bar). The tested antibody fragments were divided over 2 graphs, A and B. A's negative controls either the virus was omitted (no virus) or a non-rotavirus specific VHH was added. The non-specific VHH fragment is specific for the human pregnancy hormone hCG. Isolation of this fragment has been described (Spinelli, S., Frenken, L., Bourgeois, D., de Ron, L., Bos, W., Verrips, T., Anguille, C., Cambillau, C. and Tegoni, M. "The crystal structure of a llama heavy chain domain". Nat. Struct. Biol. (1996) 3: 752-757; Frenken, L. G. J., et al. "Isolation of antigen specific Llama VHH antibody fragments and their high level secretion by *Saccharomyces cerevisiae*". J. Biotechnol. (2000) 78, 11-21).

Hence, using this method, a number of VHH fragments were identified that can inhibit rotavirus infection in an in vitro system.

Example 3

In Vivo Rotavirus Inhibition in Mice

Some of the VHH fragments selected via the approach described in example 2 were used in in vivo experiments to study the efficacy of these antibody fragment in the prevention or treatment of rotavirus induced diarrhoea in mice. This model system has been frequently used for study of rotavirus infection (Ebina, T, Ohta, M, Kanamaru, Y, Yamamotoosumi, Y, Baba, K. "Passive immunisations of suckling mice and infants with bovine colostrum containing antibodies to human rotavirus". J Med Virol. (1992) 38: 117-123).

14 days pregnant, rotavirus negative BALB/c mice were obtained from Möllegård, Denmark. The mice were housed individually in the animal facility at Huddinge Hospital. Approval was obtained from the local ethical committee of Karolinska Institute at Huddinge Hospital, Sweden. Normal pellet diet and water was provided ad libitum.

In order to examine whether the fragments can inhibit infection when bound to rotavirus (RV), selected VHH fragments were premixed with titrated amounts (2×107 ffu) of RRV before it was used for infection on day 1.

Four-day old mice pups were treated daily with VHH fragments, including day 0 (day before infection) up to and including day 4 (FIG. 2) and diarrhoea was assessed. A marked reduction in occurrence of diarrhoea was observed for antibody fragment 2B10, shown in FIG. 2. The number of pups with diarrhoea is significantly lower at day 2 in the group receiving fragment 2B10 compared to the untreated group. Moreover, at days 3, 4 and 5 none of the pups in 2B10 treated group displayed signs of diarrhoea compared to the majority of the pups in the other RRV treated groups (FIG. 2). No statistically significant effects of the unrelated VHH fragment RR6 (directed against azo dyes; Frenken, L. G. J., et al. "Isolation of antigen specific Llama VHH antibody fragments and their high level secretion by *Saccharomyces cerevisiae*". J. Biotechnol. (2000) 78, 11-21) was found compared to the untreated group.

Additionally, the mean number of diarrhoea days per mouse pup were calculated for each treatment group as the number of diarrhoea days per pup divided by the total number of pups per treatment group. For the fragment 2B10 treated groups this was found to be significantly reduced to 0.33±0.21 days compared to 2.87±0.29 days for the untreated group.

It is important to note that from now on in the following examples the pUR5071 derived plasmid containing the gene encoding for fragment 2B10 was named pUR655 and the encoded antibody was renamed fragment VHH1.

Example 4 (a to k)

Further similar experiments separate to Examples 1 to 3 were carried out as follows:

a) Construction of Anti-Rotavirus scFv-2A10 and VHH1 Expression Vectors.

Total RNA was extracted from an anti-rotavirus mAb 2A10 (IgA class) secreting hybridoma (Giammarioli et al. (1996) Virol. 225:97-110)). Variable region encoding sequences of both the heavy (VH) and light (VK) chains were amplified using a 5' RACE kit (5' RACE System for Rapid Amplification of cDNA Ends (Version 2.0, Invitrogen™ life technologies, Carlsbad, Calif.). The primers for the 5' RACE of VH were

| | |
|---|---|
| ACRACE1: | 5'-CAGACTCAGGATGGGTAAC-3', |
| ACRACE2: | 5'-CACTTGAATGATGCGCCACTGTT-3', |
| ACRACE3: | 5'-GAGGGCTCCCAGGTGAAGAC-3', while the primers, |
| mkRACE1 | (5'-TCATGCTGTAGGTGCTGTCT-3') |
| mkRACE2 and | (5'-TCGTTCACTGCCATCAATCT-3') |
| mkRACE3 | (5'-TGGATGGTGGGAAGATGGAT-3') | were utilized to amplify the variable region of the light chain. The resulting A-tailed PCR product was cloned into a pGEMΔ-T easy vector with 3'-T overhangs and sequenced. The VH and VK sequences were fused together with a linker encoding gene (with the amino acid sequence (G4S)3). Both chains were re-amplified from the cloned 5' RACE products using the primers
ClaI-VHs
(5'-TTTTATCGATGTGCAGTTGGTGGAGTCTGG-3')
and Linker-VHas
(5'-CGATCCGCCACCGCCAGAGCCACCTCCGCCTGAACCGCCTCCACCT

GAGGAGACGGTGACCGTGG-3');

Linker-VKs
(5'-GGTGGAGGCGGTTCAGGCGGAGGTGGCTCTGGCGGTGGCGGATCGG

ACATTGTGATGACCCAGTC-3')
and

EcoRI-Vkas
(5'-TTTTGAATTCTTTTATTTCCA GCCTGGTCC-3').

The resulting VH and VK PCR products were mixed together and used as a template for a fusion PCR using the primers ClaI-VHs and EcoRI-VKas. The fused PCR products were cloned into a pGEMΔ-T easy vector after addition of overhang A using Taq DNA polymerase. The fused scFv-2A10 encoding sequence was finally cut out from the plasmids using EcoRI plus ClaI and subcloned into pBluescript II SK (+) (Stratagene, La Jolla, Calif.) containing an E-tag (pBS-E-tag).

Figure 3A:
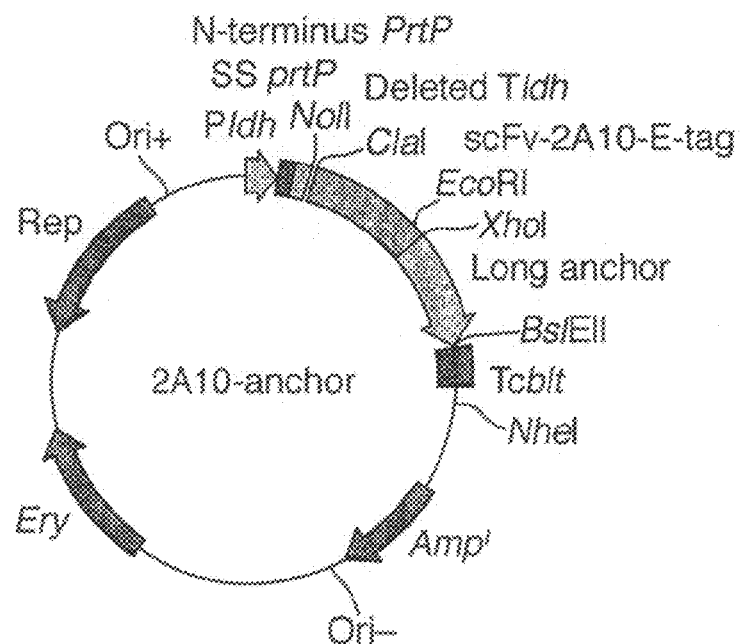
FIG. 3 shows a Map of Lactobacillus expression vectors:
(a) 2A10-anchor;
(b) VHH1-anchor, mediating surface-anchored expression of antibody fragments by fusion to the last 244 amino acids of L. casei proteinase P;
(c) 2A10-secreted; and
(d) VHH1-secreted with a stop codon (TAA) inserted after the E-tag sequence, mediating secretion of the antibody fragment.
Figure 3B:
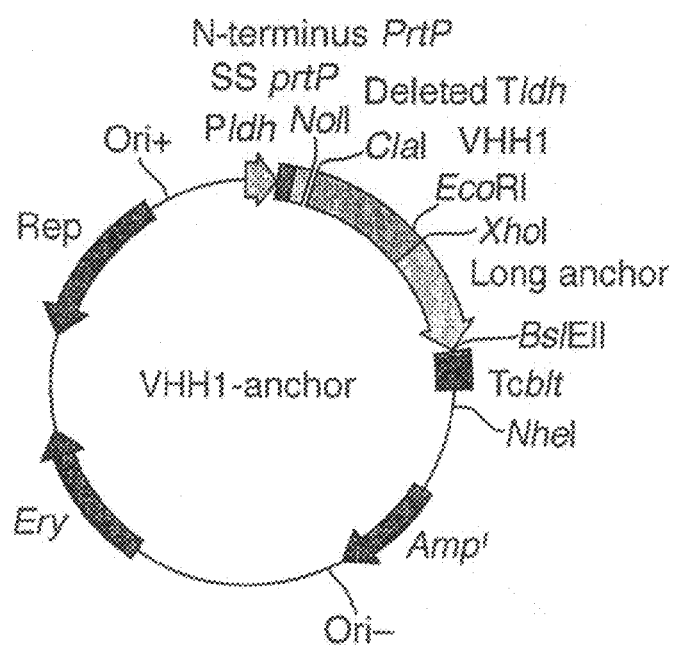
Figure 3C:
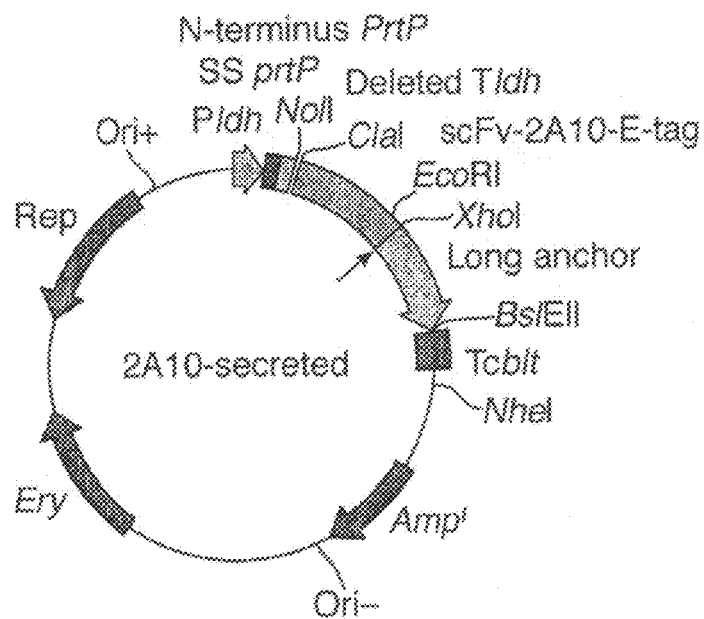
Figure 3D:
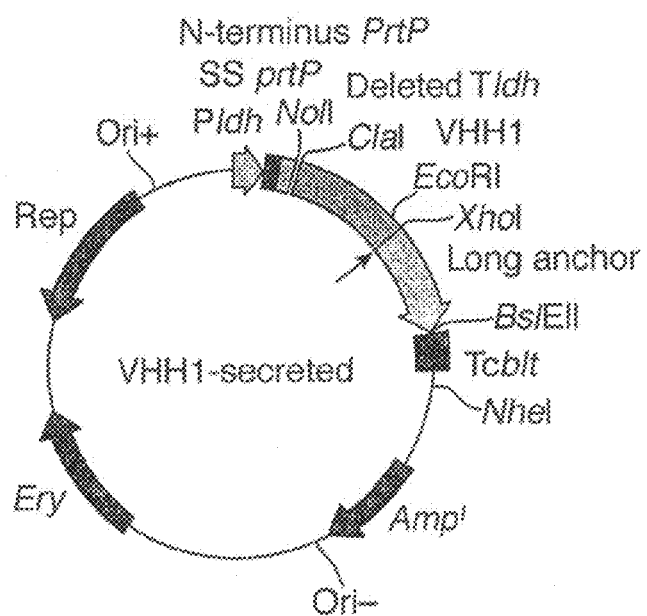

The VHH1 was amplified from pUR655 using a sense primer containing ClaI restriction site and an anti-sense primer containing EcoRI restriction site and then inserted into the pBS-E-tag vector. For generation of surface expressed antibody fragments, the scFv-2A10-E-tag and the VHH1-E-tag were excised from the pBS-E-tag vector using ClaI and XhoI restriction sites, and fused to an anchor sequence, the last 244 amino acids of the proteinase P protein of L. casei (Krüger et al, Nature Biotechnol (2002) 20:702-706), into the Lactobacillus expression vector pLP502 (FIGS. 3A and 3C). To generate the secreted antibody fragment, a stop codon (TAA) was inserted by PCR amplification after the E-tag and the products were inserted into pLP502 between the ClaI and XhoI restriction sites (FIGS. 3B and 3D). The pLP502 vector contains the constitutive promoter of the lactate dehydrogenase gene (Pldh). (Pouwels et al. "*Lactobacilli* as vehicles for targeting antigens to mucosal tissues by surface exposition of foreign antigens" Methods in Enzymology (2001) 336:369-389). Transformation into *L. paracasei* was performed as previously described (Krüger et al (2002) as above).

b) Comparison of Expression Levels of Antibody Specific Transgenes in Transformed *lactobacilli*.

Total RNA was extracted from different *lactobacilli* constructs cultured to an OD600 of 0.8 (QIAGEN) and reverse transcription was performed after digesting residual DNA with RQ1 DNase (Promega). The amount of mRNA for the different antibody fragments was measured using the qPCR core kit for SYBR® green I (MedProbe, Oslo, Norway) and ABI PRISM 7000 sequence detection system (PE Applied Biosystems, Foster City, Calif.). Typical profile times used were: initial step, 95° C., 10 minutes followed by a second step, 95° C. 15 seconds and 58° C. 1 minute, 40 cycles. Pooled cDNA was used for the generation of a standard curve for 16SrRNA and the antibody insert using the primers p0          (5'GAGAGTTTGATCCTGGCTCAG 3')
and p6          (5'CTACGGCTACCTTGTTACGA 3')

for the 16SrRNA
and primers prtpsp  (5'TCTTGCCAGTCGGCGAAAT 3')
and

XhoI-VHH    (5'CCGCTCGAGTGCGGCACGCGGTTCC 3')

for the insert.

c) Purification of Secreted Antibody Fragments.

For purification of and VHH1-secreted antibody fragments, *L. paracasei* containing the constructs were cultured to an OD600 of 0.8. After centrifugation, the pH of the supernatants was adjusted to 7 and filtered through a 0.45 μm filter. The secreted antibody fragments were subsequently purified according to the instructions provided in the RPAS Purification Module (Amersham-Bioscience, Little Chalfont, Buckinghamshire, UK). Dialysis overnight at 8 C was performed with a Spectra/Porμ membrane MWCO 6-8000 (Spectrum Medical Industries, Inc., Los Angeles, Calif.) against 1×PBS. The purified antibody fragments were run on a 15% SDS-poly acrylamide gel to verify the purity of the sample and the concentration of total protein was determined by the BioRad protein assay (BioRad Laboratories, Hercules, Calif.).

d) Protein Extraction and Determination of Protein Concentration.

*L. paracasei* containing the constructs 2A10-anchor, VHH1-anchor, 2A10-secreted, VHH1-secreted, irrelevant-secreted and irrelevant-anchor were cultured in MRS broth containing 3 μg/ml erythromycin to an OD600 of 0.8. The bacteria were lysed in 10 mM Tris-HCl pH 8.0 containing 10 mg/ml lysozyme at 37 C for one hour and then disrupted by sonication (6×30 s on/off cycles) with 60% duty cycle (Digital Sonifier, model 250, Branson Ultrasonics corporation, Danbury, Conn.). Debris was removed by centrifugation. The supernatants were concentrated 50× using ultrafiltration (Amicon, Beverly, Mass.). BioRad protein assay was used to determine the protein concentration as described above.

e) Enzyme-Linked Immunosorbent Assay and Flow Cytometry.

ELISA 96 well plates were coated with rabbit anti-human rotavirus sera (1/1000). 1:100 dilution of Rhesus rotavirus stock (RRV) was used for secondary coating. After blocking, the plates were incubated with the protein extracts or concentrated supernatants. Mouse anti-E-tag antibodies (Amersham Pharmacia Biotech, Bucks, UK) or rabbit anti-llama antibodies, horse radish (HRP) conjugated goat anti-mouse antibodies or swine anti-rabbit antibodies (DAKO A/S, Glostrup, Denmark) and 3,3',5,5'-tetramethylbenzidine substrate (TMB) were added and the absorbance was measured at 630 nm using a Vmax Microplate Reader (Molecular Devices, Sunnyvale, Calif.). All antibodies were diluted 1/1000. Purified VHH1-E-tag and monoclonal 2A10 antibodies were used as standard to determine the concentration of antibody fragments produced by the different *lactobacilli* transformants.

Flow cytometry was carried out according to standard protocols using anti-E-tag antibodies and the samples were analyzed using a FACS Calibur machine (Becton Dickinson, Stockholm, Sweden).

Results are shown in FIG. 4*a*.

f) Electron Microscopy SEM TEM.

For Scanning Electron Microscope (SEM) cultures of *lactobacilli* transformants expressing VHH1 anchored on the surface and the non-transformed *L. paracasei* were mixed with RRV and after incubation, fixed and added onto a poly-L-lysine coated RC58 coated slide. The slides were analyzed by SEM (JEOL JSM-820, Tokyo, Japan) at 15 kV.

For Transmission Electron Microscope (TEM) RRV were added onto grids, dipped in supernatant (25 times concentrated) from the *lactobacilli* expressing secreted VHH1 or supernatant from the non-transformed *L. paracasei*. Subsequently mouse anti-E-tag antibody (1:1000) and 10 nm gold labelled goat anti-mouse IgG antibodies (1:1000) (Amersham Biosciences) were added. The grids were analysed by TEM (Tecnai 10 transmission electron microscope, Fei Company, The Netherlands) at 80 KV.

Figure 4B:
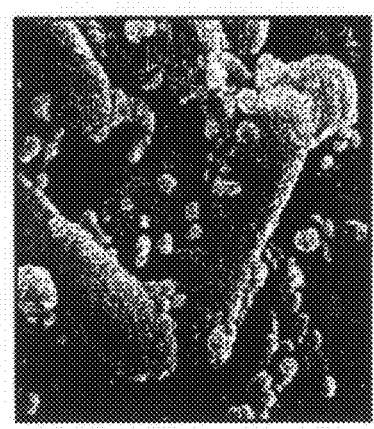

Results are shown in FIG. 4b and FIG. 11.

g) Virus Production and Purification.

Rhesus rotavirus was cultured in MA104 cells as previously described. Plaque-purified RRV was used throughout the study. A single virus stock was produced for the entire study by infecting MA104 cells with RRV at a multiplicity of infection (MOI) of 0.1 in serum-free M199 medium (Gibco Laboratories, Grand Island, N.Y.) containing 0.5 µg of trypsin (Sigma Chemical Co., St. Louis, Mo.) per ml. When the cytopathogenic effect reached approximately 75% of the monolayer, cells were freeze-thawed twice and cell lysates were cleared by low-speed centrifugation. The virus suspension was divided into aliquots and stored at −80° C. until use. Determination of virus titers was performed by an immunoperoxidase focus reduction test. A single virus stock was produced for the entire study.

h) In Vitro Neutralization Assays.

Antibody expressing *lactobacilli* were further tested for inhibitory effect on rotavirus by a microneutralization assay as described previously (Giammarioli et al 1996 as above). For anchored antibody fragments, the bacteria were serially diluted in MEM media and incubated for 1 h at 37° C. with 200 ffu of trypsin-activated RRV (100 µl). At the end of incubation, bacteria were removed by centrifugation and the supernatant was used for inoculating MA104 cell monolayers grown in 96-well plates. Concentrated culture supernatants from *lactobacilli* secreting antibody fragments, neat or diluted in MEM, were used for incubation with RRV and inoculation of MA104 cell monolayers. The inoculated plates were incubated at 37° C. for 1 hrs, washed with MEM medium, supplied with fresh MEM medium supplemented with antibiotics (gentamycin and penicillin/streptomycin) and incubated at 37° C. in a CO2 atmosphere for 18 h. Monolayers were fixed and stained with immunoperoxidase as described (Svensson et al 1991 as above). A reduction in the number of RRV-infected cells greater than 60% with respect to the number in control wells was considered to indicate neutralization. Purified VHH1 fragments produced by *lactobacilli* were used as a positive control.

Results are shown in FIG. 5.

i) In Vivo Assays.

All animal experiments were approved by the local ethical committee of the Karolinska Institutet at Huddinge Hospital, Sweden. Pregnant BALB/c female mice were purchased from Møllegard, Denmark. Four-day-old pups were used for the study. Pups were fed 10 µl of different treatments once a day, starting on day −1 until day 3. *Lactobacilli* were administered once, one day before rotavirus challenge. Infections were made orally on day 0 using 2×10⁷ pfu RRV in 10 µl volume.

Occurrence of diarrhoea was recorded daily until day 4. Pups were euthanized using intra-peritoneal pentobarbital on day 5. Sections of small intestines were stabilized in RNAlater® (QIAGEN) for RNA isolation or fixed in neutral buffered formalin for histopathological analysis or resuspended in sterile PBS for the *Lactobacillus* survival study.

Four independent experiments were conducted with various lactobodies, initially testing the dose response behaviour of the bacteria producing VHH1 anchored VHH1 fragments and subsequently testing other lactobodies at the optimal dose. Control lactobodies expressing irrelevant antibody fragments or nontransformed *lactobacilli* were included in each experiment. An infection only group was also included in each experiment.

To evaluate the survival of *lactobacilli* in the intestine of mice, pups were once fed *lactobacilli* expressing anchored VHH1 on day −1 and half of them were infected with RRV on day 0. Two pups in each group were euthanized and sections of the small intestine were removed on days 1, 3, 7, 14. The presence of transformants was determined by culturing intestinal extracts on Rogosa plates containing erythromycin (3 µg/ml). PCR was used for detection of the VHH1 insert.

Figure 6B:
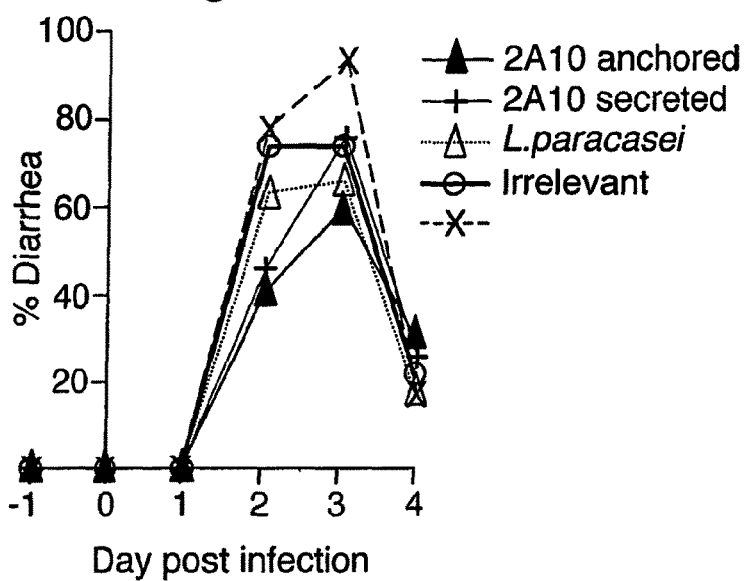

Results are shown in FIG. 6.

j) Analysis of Intestinal Specimens.

Sections of the small intestine were taken on day 4 and perfused with 4% neutral buffered formalin and Hematoxylin and Eosin staining was performed after sectioning according to standard protocols. Individual slides were evaluated blindly for typical signs of rotavirus infection.

Total cellular RNA was isolated from small intestinal tissue and was used for Real Time analysis after digestion of residual genomic DNA using RNase free DNase®. EZ RT-PCR® core reagent kit (PE Applied Biosystems, Foster City, Calif., USA) was used for Real Time PCR. A standard curve was generated using a pet28a (+) vector with the RRV vp7 gene cloned between the NcoI and XhoI restriction sites. Rotavirus vp7 mRNA or viral genomic RNA was amplified at 58° C. (ABI 7000 cycler, Applied Biosystems) in the presence of 600 nM primers, 300 nM probe, 5 mM Mn to generate a 121 bp long amplicon. The sense primer (VP7f: 5'-CCAAGGGAAAAT GTAGCAGTAATTC-3') (nucleotide (nt) 791-815), the antisense primer (VP7r: 5'-TGCCACCAT-TCTTT CCAATTAA-3'), (nt 891-912), and the probe (5'-6FAM-TAACGGCTGATCCAACCACAGCACC-TAMRA-3' (nt 843-867) were designed based on the vp7 gene sequence of rhesus rotavirus (accession number AF295303). The lowest level of detection of the PCR is 10 viral RNA copies. The RNA samples from each animal was normalized for the internal housekeeping gene control GAPDH (Overbergh et al, (1999) Cytokine 11: 305-312). Detection of no virus or less than 10 virus genomes was defined as clearance from infection.

Results are shown in FIG. 7.

k) In Situ Expression of the VHH1 Fragments on the *lactobacilli* Surface in the Feaces.

Feacal samples of three animals from the groups receiving the *lactobacilli* expressing the VHH1 anchored fragments, non-transformed *lactobacilli* or a non treated group were collected at the day of termination. The samples were smeared on a Super frost coated glass slide and fixed by methanol:acetone (1:1) for 10 minutes on ice. A mouse anti-E-tag antibody (1/200) and thereafter a cy2 labelled donkey anti-mouse antibody (1/200) was added to the slides and incubated for 1 hour under humid conditions. The surface expressed VHH1 fragments were detected by fluorescence microscope.

Statistics

The diarrhoeal illness in pups was assessed on the basis of consistency of feces. Watery diarrhoea was given a score 2 and loose stool was given a score 1, no stool or normal stool was given a score 0. The percentage of diarrhoea score was calculated each day. Total daywise score in a treatment group was compared to untreated group by Fisher's exact test.

Severity was defined as the sum of diarrhoea score for each pup during the course of the study and duration was defined as the sum of days with diarrhoea. Both severity and duration were analysed by Kruskal Wallis and Dunn tests.

Results:
Discussion of Figures and Tables achieved by *lactobacilli* produced E-tag purified VHH1 antibody (20 μg/ml). Dotted line indicates the neutralization level of 2A10 monoclonal hybridoma supernatant (147 ng/ml). Neutralization achieved by different concentrations of VHH1 anchored *lactobacilli* (■), 2A10 anchored *lactobacilli* (▣)) and non-transformed *lactobacilli* (□). FIG. 5 shows a signifi-

TABLE 2

Duration and Severity of diarrhoea in different treatment groups.

|  | Duration (mean ± SE) | P | Severity (mean ± SE) | P |
|---|---|---|---|---|
| VHH1 ank (27) | 1.222 ± 0.163 | Vs untreated <0.01 Vs irrelevant <0.05 | 1.667 ± 0.250 | Vs untreated <0.001 Vs irrelevant <0.01 |
| Untreated (30) | 2.133 ± 0.104 | — | 3.733 ± 0.1656 | — |
| L. paracasei (17) | 1.941 ± 0.200 | — | 2.882 ± 0.352 | — |
| Irrelevant VHH ank (17) | 2.118 ± 0.169 | — | 3.353 ± 0.283 | — |
| VHH1 sec (10) | 1.909 ± 0.162 | — | 2.727 ± 0.237 | — |
| 2A10 ank (10) | 2.000 ± 0.258 | — | 2.600 ± 0.3712 | — |
| 2A10 sec (10) | 2.100 ± 0.233 | — | 2.900 ± 0.233 | — |
| Preincubated VHH1 ank (10) | 1.200 ± 0.249 | — | 1.700 ± 0.395 | Vs untreated <0.01 |
| Lyophilized VHH1 ank (7) | 1.286 ± 0.285 | — | 1.857 ± 0.404 | Vs untreated <0.05 |

FIG. 4a shows the surface expression of the 2A10-scFv and VHH1 by *lactobacilli* was shown by flow cytometry using an anti-E-tag antibody A lower level of detection of the E-tag was observed on *lactobacilli* producing the 2A10 anchored fragments compared to the VHH1 anchored and irrelevant scFv and VHH control fragments expressing bacteria (data not shown).

The binding activity of the antibody fragments was analyzed by ELISA and electron microscopy. For ELISA, homogenates of 2A10-anchor- and VHH1-anchor-transformed *lactobacilli* and supernatant from the 2A10-secreted- and VHH1-secreted-transformed *lactobacilli* were tested using the E-tag for detection. Antibody fragments, VHH1-anchored, VHH1-secreted and 2A10-anchored, expressed from *lactobacilli* bound to plates coated with rotavirus. A higher level of binding was observed for the llama VHH1 fragments, both anchored and secreted (purified and from the supernatant). The amount of secreted 2A10 was too low to be detected by ELISA. The non-transformed *L. paracasei*, irrelevant antibody fragments from transformed *lactobacilli* expressing anchored or secreted scFv and anchored or secreted VHH did not bind to rotavirus (data not shown). The amount of antibody fragments produced by the VHH1-anchor transformants was calculated to be approximately $10^4$ VHH1 fragments/bacteria, and 600 2A10 fragments/bacteria (intracellular and on the surface). The VHH1-secreted transformants produced approximately 1 μg/ml of VHH1 fragments in the supernatant.

Figure 11A:
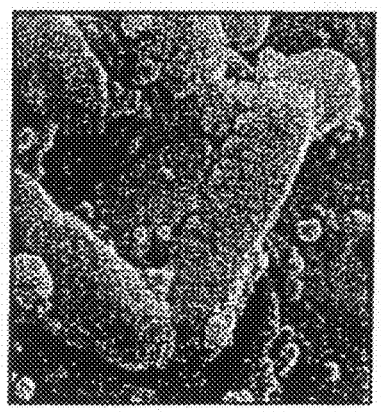
Figure 11B:
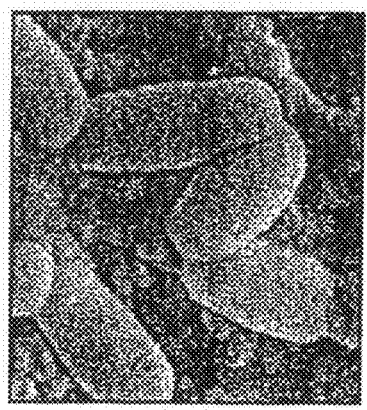

FIGS. 4b and 11a show *lactobacilli* expressing VHH1 antibody fragments on their surface, which were incubated with rotavirus and then analyzed by SEM. The results showed binding of the virus on the bacterial surface (FIGS. 4ba and 11b), but not to a non-transformed *L. paracasei* strain (FIG. 11b). Using TEM (negative staining), binding to the virus by llama antibody fragments from the supernatant of *lactobacilli* transformed with the VHH1-secreted vector could be demonstrated, whereas the non-transformed *L. paracasei* strain control supernatant did not bind rotavirus (data not shown).

The effect of *Lactobacillus* produced antibody fragments in a rotavirus neutralization assay was analysed in FIG. 5. The solid line of this figure represents neutralization level cant dose-dependent reduction of the infection in the presence of *lactobacilli* expressing surface bound VHH1 or in the presence of the supernatant containing the secreted VHH1. A slight neutralizing capacity of the supernatant from non-transformed *lactobacilli* was also observed. The 2A10-transformed *lactobacilli* (secreted and anchored) were not protective even though the supernatant of the 2A10 monoclonal hybridoma cells, containing 150 ng/ml of the antibody was 95% protective.

FIG. 6 shows the prevalence of diarrhoea in mice treated with *lactobacilli* expressing VHH1-anchored fragments. Surface VHH1 expressing *lactobacilli* significantly reduced the diarrhoea prevalence on day 2 over non transformed *lactobacilli* (P=0.0172).

FIG. 7 shows that in the untreated group, histology of the duodenum and jejunum sections reveals typical signs of rotavirus infection; swelling of villus tips, vacuolization, constriction of villus bases and unpolarized nuclei within cells (a). The groups receiving *L. paracasei* (b) or *lactobacillus* expressing VHH1-anchored (c) and the uninfected (d) shows fairly normalized histology.

FIG. 8 shows that the mean viral load in VHH1 anchored treatment group is at least 200 fold lower than untreated group. A probiotic effect of irrelevant *lactobacilli* controls was also seen (10 fold reduction in viral load). Clearance from virus was defined as no vp7 detection or detection of less than 10 vp7 RNA molecules. 27% animals were cleared of rotavirus in VHH1 anchored treatment group as compared to 9% in untreated group.

FIG. 9 shows that on day 2 dose $10^8$ CFU and $10^9$ CFU of *lactobacilli* expressing VHH1-anchored fragments cause significant reduction in diarrhea prevalence compared to untreated group, P<0.0001 and P=0.0024. Number of pups in each group: 7 each in $10^7$ CFU/dose and $10^8$ CFU/dose and 8 in $10^9$ CFU/dose and untreated.

FIG. 10 shows that a group where infections were made with RRV incubated with *lactobacilli* expressing VHH1-anchored fragments was included. Treatment in this group was continued as usual. Surface VHH1 expressing *lactobacilli* given in a freeze-dried form significantly reduced the diarrhea prevalence on day 2 compared to the untreated group (P=0.0317). On day 3, there was a significant reduction in diarrhea prevalence in groups receiving preincubated VHH1-anchored expressing *lactobacilli* (n=7; P=0.0004), lyophilized VHH1-anchored expressing *lactobacilli* (n=7; P=0.0072), VHH1-anchored expressing *lactobacilli* (n=10; P=0.0022) in comparison to the untreated group (n=10). Disease severity, in comparison to the untreated group, was also reduced when VHH1 surface expressing *Lactobacillus* was administered in a freeze-dried form (n=10; P<0.01) or when infections were made with RRV preincubated with a fresh culture of these bacteria for 2 h (P<0.05).

In Situ Expression of VHH1 Fragments on the *lactobacilli* Surface in Faeces (Example 4 (k) results)

Faecal samples of three animals from the groups receiving *lactobacilli* expressing the VHH1 anchored fragments, untreated group and negative control mice were collected on day 4, the day of termination, for determination of in situ expression of the VHH1 anchored fragments. *Lactobacilli* expressing VHH1 could be detected using fluorescent anti-E-tag antibody in the of treated mice. No staining could be observed in the control group (data not shown).

Survival of *lactobacilli* in the Mouse Intestine

Pups were fed *lactobacilli* expressing the anchored VHH1 against rotavirus once (on day 0) and half of them were subsequently infected with RRV on day 1. Two pups in each group were sacrificed every second day and checked for the presence of *Lactobacillus* transformants by culturing of the intestinal content. The bacteria could be detected in the duodenum and the ileum 48 h post treatment with no difference between the rotavirus infected and uninfected groups, whereas at 96 h post treatment, no transformants could be detected (data not shown).

The Efficacy of *Lactobacillus* Transformants to Reduce Diarrhea in a Rotavirus Infection Model The therapeutic effect of the transformed *lactobacilli* was tested in a mouse pup model of rotavirus-induced diarrhea. Pups were orally fed *lactobacilli* expressing the 2A10-scFv or the VHH1 in secreted or anchored forms during five days (day −1 to 3) and infected with RRV on day 0. Control groups included non-transformed *L. paracasei* and bacteria expressing an irrelevant anchored VHH antibody fragment. 108 CFU as the optimal dose for diarrhea intervention (FIG. 9). The surface VHH1 expressing bacteria shortened the disease duration (normal duration 1.2 days) by approximately 0.9 days (P<0.01) and by 0.7 days compared to mice treated with non-transformed *L. paracasei* (P<0.05). The severity of the diarrhea was also reduced from 3.7 to 1.7 in mice treated with surface VHH1 expressing *lactobacilli* as compared to the disease severity in untreated pups (P<0.001) and by a factor of 1.2 in comparison to pups treated with non-transformed *L. paracasei* (P<0.01). A minor probiotic effect by the non-transformed *lactobacilli* was also observed (Table 2). In addition, the diarrhea prevalence was significantly lowered both on days 2 and 3 in mice treated with the *Lactobacillus* expressing surface VHH1 in comparison to untreated mice (P<0.0001, for both days) or mice treated with non-transformed *L. paracasei* (P<0.02, for day 2) (FIG. 6a). The constructs expressing the secreted or anchored 2A10 as well as the secreted VHH1 did not induce significantly higher protection than non-transformed *lactobacilli* (FIG. 6a,b). Disease severity, in comparison to the untreated group, was also reduced when VHH1 surface expressing *Lactobacillus* was administered in a freeze dried form (P<0.01) or when infections were made with RRV preincubated with a fresh culture of these bacteria for 2 h (P<0.05) (Table 2 and FIG. 5).

Figure 7A:
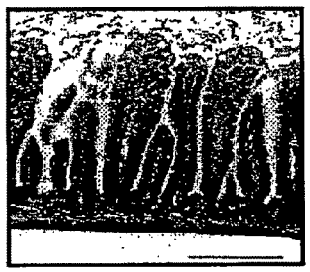
Figure 7B:
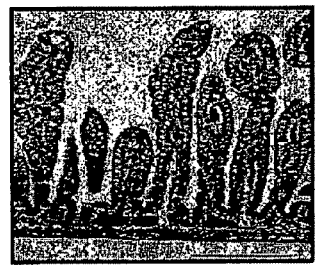
Figure 7C:
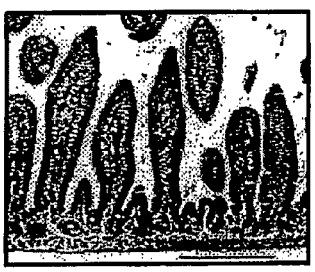
Figure 7D:
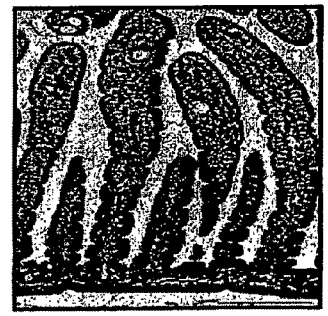

Histological examination of proximal small intestine sections on day 4 revealed a marked reduction of pathological changes in rotavirus infected animals treated with surface VHH1 expressing *lactobacilli* and in some mice, the histology was completely normalized. The histology in the group receiving no *lactobacilli* revealed typical signs of rotavirus infection with swelling of villus tips, constriction of villus bases, vacuolization and irregularly placed cell nuclei (FIG. 7a,b,c,d). To assess whether there was a reduction in viral replication in the enterocytes, a real time PCR for expression of the rotavirus vp7 gene was developed. The mean viral load in animals receiving *lactobacilli* expressing surface bound VHH1 antibody fragments was at least 250 fold lower than in untreated mice. *Lactobacilli* expressing an irrelevant VHH fragment also reduced the viral vp7 load (up to 10 fold). The clearance rate was 27% in the group given *lactobacilli* expressing surface anchored VHH1 as compared to 9% in the untreated group (FIG. 8).

These experiments show the successful expression of llama derived VHH antibody fragment (VHH1) and scFv (scFv-2A10) against rotavirus both on the surface of *Lactobacillus casei* 393 pLZ15 and as a secreted protein. Efficacy of these recombinant *lactobacilli* in the treatment of rotavirus by in vitro neutralization and in an infant mouse infection model has also been demonstrated.

Example 5

Calcium Alginate Encapsulation of Anti-Rotavirus VHH

A solution of 2% sodium alginate was added dropwise to a solution of 0.1 M calcium chloride, containing 1% of the VHH, resulting in the formation of calcium alginate beads (with a size of about 2 mm). The dispersion was allowed to stand for 30 min for the calcium alginate beads to settle at the bottom of the beaker. The beads were then collected with a sieve and washed once with water Example 6

Compositions and Preparations of Ice Creams Containing Encapsulated Anti-Rotavirus VHH or a *Lactobacillus* Producing this VHH.

An ice cream composition was prepared having the following formulation;

|  | weight % |
|---|---|
| Sucrose | 13.000 |
| Skimmed Milk Powder | 10.000 |
| Butter fat | 8.000 |
| Maltodextrin 40 | 4.000 |
| Monoglycerol Palmitate (MGP) | 0.300 |
| Locust Bean Gum | 0.144 |
| Carageenan L100 | 0.016 |
| Flavour | 0.012 |

Encapsulated VHH solution at a volume resulting in between 5 and 5000 microgram of VHH per serving.

| Water | to 100 |
|---|---|
| Total soluble solids; | 35% by weight |
| Ice content at −18° C.; | 54% by weight |

All the ice cream ingredients were mixed together using a high shear mixer for approximately 3 minutes. The water being added at a temperature of 80° C. The temperature of the water ice mix was approximately 55-65° C. after mixing.

The mix was then homogenized (2000 psi) and passed through to a plate heat exchanger for pasteurization at 81° C. for 25 seconds. The mix was then cooled to approximately 4° C. in the plate heat exchanger prior to use.

Alternatively, an anti-rotavirus VHH producing *Lactobacillus* strain can be added Instead of the encapsulated VHH solution, preferably in a concentration of 109 per serving or higher.

The ice cream pre-mix was then frozen using a Technohoy MF 75 scraped surface heat exchanger, no overrun was introduced into the ice cream. The ice cream was extruded at a temperature of from 4.4° C. to −5.4° C. The product was then hardened in a blast freezer at −35° C., then stored at −25° C.

A water ice solution having the following composition was prepared as follows;

| | % by weight |
|---|---|
| Sucrose | 25 |
| Locust Bean Gum | 0.5 |

Encapsulated VHH solution at a volume resulting in between 5 and 5000 microgram of VHH per serving.

| | |
|---|---|
| water | to 100 |
| Total soluble solids; | 25.5% by weight |
| Ice content at −18° C.; | 62% by weight |

All the water ice ingredients were mixed together using a high shear mixer for approximately 3 minutes. The water being added at a temperature of 80° C. The temperature of the water ice mix was approximately 55-65° C. after mixing.

The mix was then homogenized (2000 psi) and passed through to a plate heat exchanger for pasteurization at 81° C. for 25 seconds. The mix was then cooled to approximately 4° C. in the plate heat exchanger prior to use.

Instead of the encapsulated VHH solution at this moment also a anti-rotavirus VHH producing *Lactobacillus* strain can be added preferably in a concentration of 109 per serving or higher.

The water ice solution was frozen in a Technohoy MF 75 scraped surface heat exchanger with an overrun (volume fraction of air) of 30%. The water ice was extruded at a temperature of from −3.8° C. to −4.5° C. The product was then hardened in a blast freezer at −35° C., and stored at −25° C.

Example 7

Compositions for Spreads Containing Encapsulated Anti-Rotavirus VHH or a *Lactobacillus* Producing this VHH.

Spreads were made according to standard procedure as known in the art, using the compositions as given in Table 3.

TABLE 3

Spread compositions

| Component | Amount (wt. %) Example 1 | Amount (wt. %) Example 2 | Amount (wt. %) Example 3 | Amount (wt. %) Example 4 |
|---|---|---|---|---|
| Fat blend | 39.71 | 39.71 | 39.71 | 39.71 |
| Bolec ZT | 0.05 | 0.05 | 0.05 | 0.05 |
| Hymono 8903 | 0.16 | 0.16 | 0.16 | 0.16 |
| β-carotene (1% in Sunflower oil) | 0.08 | 0.08 | 0.08 | 0.08 |
| Total fat phase | 40.00 | 40.00 | 40.00 | 40.00 |
| Tap water | up to 60 | up to 60 | up to 60 | up to 60 |
| Sour whey powder | 0.27 | 0.27 | 0.27 | 0.27 |
| NaCl | 0.48 | 0.48 | 0.48 | 0.48 |
| K-sorbate | 0.12 | 0.12 | 0.12 | 0.12 |
| Gelatin | 1.10 | 1.10 | 1.10 | 1.10 |
| Citric acid | To pH 4.6 | To pH 5.0 | To pH 4.6 | To pH 5.0 |
| Xanthan gum | 0.10 | 0.10 | 0.10 | 0.10 |
| Calcium salt TCP C13-13 | | | 1.27 | 1.27 |
| CaSO4•0.5H2O | 1.74 | 1.74 | | |
| PH waterphase set | 4.6 | 5.0 | 4.6 | 5.0 |
| Encapsulated VHH sol. | 5-5000 | 5-5000 ug | 5-5000 ug | 5-5000 ug |
| Total water phase | To 100 | To 100 | To 100 | To 100 |
| Total | 100.00 | 100.00 | 100.00 | 100.00 |

Instead of the encapsulated VHH solution after the last heating step also a anti-rotavirus VHH producing *Lactobacillus* strain can be added aseptically, preferably in a concentration of 109 per serving or higher.

Example 8

Compositions and Preparations of Dressings Containing Encapsulated Anti-Rotavirus VHH.

To prepare a dressing the bacterial strain is cultured in a suitable food raw material (e.g. milk) to achieve a high density of the culture and sufficient production of the VHH. The cultured raw material is mixed with the typical ingredients of dressings (like oil, vinegar, egg yolk, salt) at a level that supports efficacy of the VHH and subjected to standard processing of mayonnaise, like mixing and homogenisation. Alternatively, the typical ingredients of dressings like oil, vinegar, egg yolk, salt are first mixed and subjected to a heat treatment and homogenisation followed by the addition of the cultured raw material. In stead of a VHH producing microorganism, encapsulated anti-rotavirus VHH, obtained according to example 5 can be added.

The invention claimed is:

1. A delivery system for delivering antibodies to the gastrointestinal tract comprising a probiotic lactic acid bacterium transformed with a gene encoding heavy chain immunoglobulins of the VHH type or fragments thereof derived from llama which neutralize rotavirus and have an amino acid sequence with at least 85% percent sequence identity to SEQ ID NO: 1, or comprise SEQ ID NO: 1, 2, 3, 4, 12, 14, 17, 19 and 20, wherein expression of the immunoglobulins or fragments thereof in the gastrointestinal tract following administration to a subject in need thereof inhibits rotavirus infection in the gut of the subject.

2. The delivery system as claimed in claim 1 wherein the delivery system is encapsulated in a capsule.

3. The delivery system of claim 1 wherein the pro-biotic lactic acid bacterium is Lactobacillus or Bifidobacterium.

4. The delivery system of claim 1 wherein the probiotic lactic acid bacterium is Lactobacillus casei.

5. The delivery system of claim 1 wherein the immunoglobulins of the VHH type or fragments thereof are expressed on the surface of the transformed probiotic lactic acid bacterium.

6. The delivery system of claim 1, wherein the immunoglobulin of the VHH type has an amino acid sequence as set forth in SEQ ID NO: 1.

7. The delivery system of claim 1, wherein the immunoglobulin of the VHH type has an amino acid sequence as set forth in SEQ ID NO: 2.

8. The delivery system of claim 1, wherein the immunoglobulin of the VHH type has an amino acid sequence as set forth in SEQ ID NO: 3.

9. The delivery system of claim 1, wherein the immunoglobulin of the VHH type has an amino acid sequence as set forth in SEQ ID NO: 4.

10. The delivery system of claim 1, wherein the immunoglobulin of the VHH type has an amino acid sequence as set forth in SEQ ID NO: 12.

11. The delivery system of claim 1, wherein the immunoglobulin of the VHH type has an amino acid sequence as set forth in SEQ ID NO: 14.

12. The delivery system of claim 1, wherein the immunoglobulin of the VHH type has an amino acid sequence as set forth in SEQ ID NO: 17.

13. The delivery system of claim 1, wherein the immunoglobulin of the VHH type has an amino acid sequence as set forth in SEQ ID NO: 19.

14. The delivery system of claim 1, wherein the immunoglobulin of the VHH type has an amino acid sequence as set forth in SEQ ID NO: 20.

15. The delivery system of claim 1, wherein the immunoglobulin of the VHH type has an amino acid sequence with at least 95% percent sequence identity to SEQ ID NO: 1.

16. A method for delivering antibodies to the gut in the treatment of rotavirus infections using a micro-organism transformed with the gene encoding for heavy chains immunoglobulins of the VHH type or fragments thereof, comprising administering the delivery system of claim 1 to the gut of the human or animal in need of therapy such that the heavy chain immunoglobulins of the VHH type, or fragments thereof, are expressed and/or secreted in the gut.

17. The method of claim 16 wherein the heavy chain immunoglobulin or fragments thereof of the VHH type are specific to rotavirus.

* * * * *

SEQUENCE LISTING

<160> NUMBER OF SEQ ID NOS: 23

<210> SEQ ID NO 1
<211> LENGTH: 123
<212> TYPE: PRT
<213> ORGANISM: Lama glama

<400> SEQUENCE: 1

```
Gln Val Gln Leu Gln Asp Ser Gly Gly Gly Leu Val Gln Ala Gly Asp
1               5                   10                  15

Arg Leu Ser Leu Ser Cys Ala Ala Ser Gly Arg Thr Phe Ser Ser Tyr
            20                  25                  30

Asp Met Ala Trp Phe Arg Gln Ala Pro Gly Lys Glu Arg Glu Phe Val
        35                  40                  45

Ala Ala Ile Thr Thr Ser Glu Gly Thr Trp Tyr Gly Asp Ala Gly Lys
    50                  55                  60

Gly Arg Phe Thr Ile Ala Arg Val Asn Ala Lys Asn Thr Val Tyr Leu
65                  70                  75                  80

His Met Asn Arg Leu Lys Pro Glu Asp Thr Ala Val Tyr Tyr Cys Ala
                85                  90                  95

Ala Ser Asn Gln Gly Gly Ser Leu Gln Ile Ser Thr Asn Tyr Asn Tyr
            100                 105                 110

Trp Gly Gln Gly Thr Gln Val Thr Val Ser Ser
        115                 120
```

<210> SEQ ID NO 2
<211> LENGTH: 123
<212> TYPE: PRT
<213> ORGANISM: Lama glama

<400> SEQUENCE: 2

```
Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Val Ser Ser Ser Asn Ser Pro Trp Tyr Gly Asp Ser Ile Lys
    50                  55                  60

Gly Arg Ser Thr Ile His Arg Asp Asn Ala Lys Asn Thr Val Tyr Leu
65                  70                  75                  80

Tyr Met Asn Asn Leu Lys Pro Glu Asp Thr Ala Val Tyr Tyr Cys Ala
                85                  90                  95

Ala Asp Leu Glu Gly Glu Arg Leu Gly Glu Ser Ser Tyr Asp Tyr
            100                 105                 110

Trp Gly Gln Gly Thr Gln Val Thr Val Ser Ser
        115                 120
```

<210> SEQ ID NO 3
<211> LENGTH: 127
<212> TYPE: PRT
<213> ORGANISM: Lama glama

<400> SEQUENCE: 3

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Lys Tyr Tyr
            20                  25                  30

Ala Met Ser Trp Val Arg Gln Ala Pro Gly Lys Gly Leu Glu Trp Val
        35                  40                  45

Ser Tyr Ile Asn Asp Asn Gly Gly Tyr Thr Tyr Asp Ser Asp Ser Val
    50                  55                  60

Lys Gly Arg Phe Thr Ile Ser Arg Asp Asn Ala Lys Asn Thr Leu Tyr
65                  70                  75                  80
```

```
Leu His Met Asn Arg Leu Lys Pro Glu Asp Thr Ala Val Tyr Phe Cys
                85                  90                  95

Ala Lys Trp Asp Thr Asp Ala Val Ser Ser Arg Tyr Lys Thr His
            100                 105                 110

Asn Gly Asp Ile Arg Gly Pro Gly Thr Gln Val Thr Val Ser Ser
        115                 120                 125

<210> SEQ ID NO 4
<211> LENGTH: 123
<212> TYPE: PRT
<213> ORGANISM: Lama glama

<400> SEQUENCE: 4

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Gln Phe Val
        35                  40                  45

Ala Ala Val Ser Ser Ser Asp Ser Pro Trp Tyr Gly Asp Ser Met Lys
    50                  55                  60

Gly Arg Ser Thr Ile His Arg Asp Asn Ala Lys Asn Thr Val Tyr Leu
65                  70                  75                  80

Tyr Met Asn Asn Leu Lys Pro Glu Asp Thr Ala Val Tyr Tyr Cys Ala
                85                  90                  95

Ala Asp Leu Glu Gly Glu Arg Leu Gly Glu Ser Ser Gly Tyr Asp Tyr
            100                 105                 110

Trp Gly Gln Gly Thr Gln Val Thr Val Ser Ser
        115                 120

<210> SEQ ID NO 5
<211> LENGTH: 125
<212> TYPE: PRT
<213> ORGANISM: Lama glama

<400> SEQUENCE: 5

Gln Val Gln Leu Gln Glu Ser Gly Gly Gly Leu Val Gln Ala Gly Asp
1               5                   10                  15

Ser Leu Arg Leu Ser Cys Ala Ala Ser Gly Gly Ala Leu Tyr Asp Met
            20                  25                  30

Ala Trp Phe Arg Gln Ala Pro Gly Lys Glu Arg Glu Phe Val Ala Val
            35                  40                  45

Ile Ser Tyr Asp Gly Ser Ala Thr Ser Tyr Arg Asp Ser Val Lys Gly
    50                  55                  60

Arg Phe Thr Ile Ser Arg Glu Asn Ala Lys Asn Met Ala Arg Asn Met
65                  70                  75                  80

Ala Tyr Leu Gln Met Asn Ala Leu Lys Pro Glu Asp Thr Ala Val Tyr
                85                  90                  95

Tyr Cys Ala Ala Lys Gly Pro Thr Gly Thr Leu His Thr Ser Gly Tyr
            100                 105                 110

Arg Ile Trp Gly Gln Gly Thr Gln Val Thr Val Ser Ser
        115                 120                 125

<210> SEQ ID NO 6
<211> LENGTH: 125
<212> TYPE: PRT
<213> ORGANISM: Lama glama
```

<400> SEQUENCE: 6

```
Gln Val Gln Leu Gln Glu Ser Gly Gly Gly Leu Val Gln Ala Gly Asp
1               5                   10                  15

Ser Leu Arg Leu Ser Cys Ala Ala Ser Gly Gly Ala Leu Tyr Asp Met
            20                  25                  30

Ala Trp Phe Arg Gln Ala Pro Gly Lys Glu Arg Glu Phe Val Ala Val
        35                  40                  45

Ile Ser Tyr Asp Gly Ser Ala Thr Ser Tyr Arg Asp Ser Val Lys Gly
    50                  55                  60

Arg Phe Thr Ile Ser Arg Glu Asn Ala Lys Asn Met Ala Arg Asn Met
65                  70                  75                  80

Ala Tyr Leu Gln Met Asn Ala Leu Lys Pro Glu Asp Thr Ala Val Tyr
                85                  90                  95

Tyr Cys Ala Ala Lys Gly Pro Thr Gly Thr Leu His Thr Ser Gly Tyr
            100                 105                 110

Arg Ile Trp Gly Gln Gly Thr Gln Val Thr Val Ser Ser
        115                 120                 125
```

<210> SEQ ID NO 7
<211> LENGTH: 126
<212> TYPE: PRT
<213> ORGANISM: Lama glama

<400> SEQUENCE: 7

```
Gln Val Gln Leu Gln Glu Ser Gly Gly Gly Leu Val Arg Pro Gly Gly
1               5                   10                  15

Ser Leu Arg Leu Thr Cys Ala Thr Ser Gly Phe Ser Leu Asp Tyr Tyr
            20                  25                  30

Pro Ile Ala Trp Phe Arg Gln Ala Pro Gly Lys Glu Arg Glu Gly Leu
        35                  40                  45

Ser Cys Ile Ser Ser Ser Asp Gly Gly Ala Tyr Tyr Gly Asp Ala Val
    50                  55                  60

Lys Gly Arg Phe Thr Met Ser Arg Asp Ser Ala Glu Asn Thr Val Tyr
65                  70                  75                  80

Leu His Met Asn Ser Leu Lys Pro Glu Asp Thr Ala Val Tyr Tyr Cys
                85                  90                  95

Ala Thr Ser Lys Arg Tyr Trp Arg Asn Cys Asp Val Thr Asp Tyr Asp
            100                 105                 110

Tyr His Tyr Trp Gly Gln Gly Thr Gln Val Thr Val Ser Ser
        115                 120                 125
```

<210> SEQ ID NO 8
<211> LENGTH: 126
<212> TYPE: PRT
<213> ORGANISM: Lama glama

<400> SEQUENCE: 8

```
Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Ser Leu Asp Tyr Tyr
            20                  25                  30

Pro Ile Ala Trp Phe Arg Gln Ala Pro Gly Lys Glu Arg Glu Gly Leu
        35                  40                  45

Ser Cys Val Ser Ser Ser Asp Gly Gly Thr Tyr Tyr Gly Asp Ala Ala
    50                  55                  60

Lys Gly Arg Phe Thr Met Ser Arg Asp Ser Ala Glu Asn Thr Val Thr
65                  70                  75                  80
```

Leu His Met Asn Ser Leu Lys Pro Glu Asp Thr Ala Val Tyr Tyr Cys
                    85                  90                  95

Ala Thr Ser Lys Arg Tyr Trp Arg Asn Cys Asp Val Thr Asp Tyr Asp
                100                 105                 110

Tyr His Tyr Trp Gly Gln Gly Thr Gln Val Thr Val Ser Ser
            115                 120                 125

<210> SEQ ID NO 9
<211> LENGTH: 126
<212> TYPE: PRT
<213> ORGANISM: Lama glama

<400> SEQUENCE: 9

Gln Val Gln Leu Gln Glu Ser Gly Gly Gly Leu Val Gln Ala Gly Asp
1               5                   10                  15

Ser Leu Thr Leu Ser Cys Ala Val Ser Gly Gly Thr Leu Ser Met Phe
                20                  25                  30

Ser Met Gly Trp Phe Arg Gln Ala Pro Gly Leu Glu Arg Glu Phe Val
            35                  40                  45

Ala Ile Ile Asn Asp Arg Glu Ser Ile Arg Arg Tyr Gln Asp Ser Val
        50                  55                  60

Lys Gly Arg Phe Thr Ile Ser Lys Asp Asn Ala Lys Asn Leu Val Tyr
65                  70                  75                  80

Leu Gln Met Asn Asn Leu Lys Pro Val Asp Thr Ala Val Tyr Tyr Cys
                    85                  90                  95

Ala Ala Asp Thr Thr Tyr Pro Ala Val Ala Pro Thr Ser Val Gly Gln
                100                 105                 110

Tyr Asp Tyr Trp Gly Gln Gly Thr Gln Val Thr Val Ser Ser
            115                 120                 125

<210> SEQ ID NO 10
<211> LENGTH: 125
<212> TYPE: PRT
<213> ORGANISM: Lama glama

<400> SEQUENCE: 10

Gln Val Gln Val Gln Lys Ser Glu Gly Gly Leu Val Gln Pro Gly Gly
1               5                   10                  15

Ser Leu Arg Leu Ser Cys Ala Val Ser Gly Arg Thr Asp Ser Ile Ser
                20                  25                  30

Ala Met Gly Trp Phe Arg Gln Ala Pro Gly Lys Glu Arg Glu Phe Val
            35                  40                  45

Val Ala Ile Arg Trp Ile Glu Gly Gly Thr Trp Tyr Gly Asp Pro Ala
        50                  55                  60

Ala Gly Arg Phe Thr Ile Ala Arg Asp Ile Ala Lys Asn Thr Gly Tyr
65                  70                  75                  80

Leu Gln Met Asn Arg Leu Asn Pro Asp Asp Thr Ala Val Tyr Phe Cys
                    85                  90                  95

Ala Ala Ala Lys Phe Gly Pro Ser Lys Leu Gln Phe Ser Gln Gly Tyr
                100                 105                 110

Asp Tyr Trp Gly Gln Gly Thr Gln Val Thr Val Ser Ser
            115                 120                 125

<210> SEQ ID NO 11
<211> LENGTH: 118
<212> TYPE: PRT
<213> ORGANISM: Lama glama

-continued

<400> SEQUENCE: 11

Gln Val Lys Leu Ala Gly Thr Leu Gly Leu Val Gln Leu Gly Asp
1               5                   10                  15

Ser Leu Gln Leu Ser Cys Val Ala Ser Gly Arg Thr Asp Val Met Gly
            20                  25                  30

Trp Phe Arg Gln Ala Pro Gly Lys Glu Arg Glu Phe Ala Ala Ile
        35                  40                  45

Thr Gly Ser Asp Gly Thr Phe Tyr Gly Asp Ala Gly Arg Gly Arg Phe
    50                  55                  60

Thr Ile Ala Arg Asp Asn Thr Lys Asn Thr Val Tyr Leu Asn Leu Asn
65                  70                  75                  80

Arg Leu Lys Pro Glu Asp Thr Ala Val Tyr Tyr Cys Ala Ala Asp Gly
                85                  90                  95

Ser Pro Leu Gln Ile Ala Ser Thr Tyr Lys Tyr Trp Gly Gln Gly Thr
            100                 105                 110

Gln Val Thr Val Ser Ser
        115

<210> SEQ ID NO 12
<211> LENGTH: 124
<212> TYPE: PRT
<213> ORGANISM: Lama glama

<400> SEQUENCE: 12

Gln Val Gln Leu Gln Asp Ser Gly Gly Gly Leu Val Gln Ala Gly Thr
1               5                   10                  15

Ser Leu Arg Leu Ser Cys Val Ala Lys Gly Gly Leu Tyr Gly Leu Gly
            20                  25                  30

Trp Phe Arg Gln Ala Pro Gly Lys Glu Arg Glu Phe Val Ala Ala Ile
        35                  40                  45

Ser Gly Ser Gly Gly Ser Thr Tyr Tyr Gly Asp Ser Val Arg Gly Arg
    50                  55                  60

Phe Thr Ile Ser Arg Asp Asn Thr Lys Asn Thr Met Tyr Leu Gln Met
65                  70                  75                  80

Asn Ser Leu Lys Pro Glu Asp Thr Ala Ile Tyr Phe Cys Ala Ala Arg
                85                  90                  95

Thr Gln Tyr Ser Ala Ser Asp Tyr Trp Trp Gln Gln Gly Glu Tyr Gly
            100                 105                 110

Tyr Trp Gly Gln Gly Thr Gln Val Thr Val Ser Ser
        115                 120

<210> SEQ ID NO 13
<211> LENGTH: 127
<212> TYPE: PRT
<213> ORGANISM: Lama glama

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Tyr Tyr
            20                  25                  30

Ala Met Ser Trp Val Arg Gln Ala Pro Gly Lys Gly Leu Glu Trp Val
        35                  40                  45

Ser Tyr Ile Asn Ser Asp Gly Gly Tyr Thr Tyr Ala Asp Ser Val
    50                  55                  60

Lys Gly Arg Phe Ile Ile Ser Arg Asp Asn Ala Lys Asn Ile Leu Tyr
65                  70                  75                  80

```
Leu His Met Asn Ser Leu Lys Pro Glu Asp Thr Ala Val Tyr Phe Cys
                85                  90                  95

Ala Lys Trp Arg Thr Asp Ala Val Ser Ser Arg Tyr Lys Thr Asn
            100                 105                 110

Asp Tyr Glu Tyr Arg Gly Pro Gly Thr Gln Val Thr Val Ser Ser
            115                 120                 125

<210> SEQ ID NO 14
<211> LENGTH: 125
<212> TYPE: PRT
<213> ORGANISM: Lama glama

<400> SEQUENCE: 14

Gln Val Gln Leu Gln Lys Ser Gly Gly Gly Leu Val Gln Ala Gly Gly
1               5                   10                  15

Ser Leu Arg Leu Ser Cys Ala Arg Gly Ser Gly Thr Phe Ser Pro Tyr
            20                  25                  30

Ala Met Gly Trp Phe Arg Gln Ala Pro Gly Glu Glu Arg Gln Phe Val
            35                  40                  45

Ala Ala Ile Thr Trp Ser Ser Asp Ser Pro Trp Tyr Gly Asp Ser Ala
        50                  55                  60

Lys Gly Arg Cys Thr Ile Ala Arg Asp Ile Thr Lys Asn Thr Val Tyr
65                  70                  75                  80

Leu Asn Ile Phe Gly Leu Lys Pro Glu Asp Thr Ala Val Tyr Tyr Cys
                85                  90                  95

Ala Glu Ser Ser Gly Ala Thr Tyr Gly Leu Ala Leu Pro Ser Ala Tyr
            100                 105                 110

Glu His Trp Gly Arg Gly Thr Gln Val Thr Ala Ser Ser
            115                 120                 125

<210> SEQ ID NO 15
<211> LENGTH: 127
<212> TYPE: PRT
<213> ORGANISM: Lama glama

<400> SEQUENCE: 15

Gln Val Gln Gly Ala Gly Leu Trp Gly Gly Leu Val Gln Leu Gly Gly
1               5                   10                  15

Ser Leu Arg Leu Ser Cys Ala Ala Ser Gly Phe Thr Phe Gly Tyr Tyr
            20                  25                  30

Ala Met Ser Trp Val Arg Gln Ala Pro Gly Lys Gly Leu Glu Trp Val
            35                  40                  45

Ser Tyr Ile Asn Asp Asn Gly Gly Tyr Thr Ala Tyr Thr Asp Pro Val
        50                  55                  60

Lys Gly Arg Phe Thr Ile Ser Arg Asp Asn Ala Lys Asn Ile Leu Tyr
65                  70                  75                  80

Leu His Met Asn Asn Leu Lys Pro Glu Asp Thr Ala Val Tyr Phe Cys
                85                  90                  95

Ala Lys Trp Gly Thr Asp Ala Val Ser Ser Arg Tyr Lys Ser His
            100                 105                 110

Asp Tyr Asp Ser Arg Gly Pro Gly Thr Gln Val Thr Val Ser Ser
            115                 120                 125

<210> SEQ ID NO 16
<211> LENGTH: 125
<212> TYPE: PRT
<213> ORGANISM: Lama glama
```

-continued

<400> SEQUENCE: 16

```
Gln Val Gln Leu Gln Glu Ser Gly Glu Gly Leu Val Gln Ala Gly Ala
1               5                   10                  15

Ser Leu Lys Leu Ser Cys Glu Ala Ser Leu Gly Gly Leu Tyr Gly Met
            20                  25                  30

Gly Trp Phe Arg Gln Ala Pro Gly Lys Glu Arg Glu Phe Val Ala Ala
        35                  40                  45

Ile Ser Gly Ser Gly Gly Thr Thr Tyr Tyr Glu Asp Ser Val Arg Gly
    50                  55                  60

Arg Phe Thr Ile Ser Arg Asp Asn Ala Lys Ser Thr Val Phe Leu Gln
65                  70                  75                  80

Met Asn Asn Leu Lys Pro Glu Asp Thr Ala Val Tyr Tyr Cys Ala Ala
                85                  90                  95

Arg Thr Ser Tyr Ser Ala Ser Asn Ala Trp Asn Gln Leu Arg Glu Tyr
            100                 105                 110

Gly Tyr Trp Gly Gln Gly Thr Gln Val Thr Val Ser Ser
        115                 120                 125
```

<210> SEQ ID NO 17
<211> LENGTH: 122
<212> TYPE: PRT
<213> ORGANISM: Lama glama

<400> SEQUENCE: 17

```
Gln Val Gln Leu Gln Glu Ser Gly Gly Gly Leu Val Gln Ala Gly Gly
1               5                   10                  15

Ser Leu Arg Leu Ser Cys Ala Gly Val Gly Arg Thr Ile Ser Pro Tyr
            20                  25                  30

Asn Met Gly Trp Phe Arg Gln Ala Leu Gly Lys Glu Arg Asp Phe Val
        35                  40                  45

Ala Ala Ile Arg Trp Ser Gly Ser Asp Thr Asn Tyr Ala Asp Ser Val
    50                  55                  60

Lys Gly Arg Phe Thr Ile Ser Arg Asp Asn Ala Glu Asn Thr Val Tyr
65                  70                  75                  80

Leu Gln Met Arg Asn Leu Asn Pro Glu Asp Thr Ala Val Tyr Tyr Cys
                85                  90                  95

Ala Ala Gly Gly Asp Val Phe Ser Ala Leu Thr Tyr His His Trp
            100                 105                 110

Gly Gln Gly Thr Gln Val Thr Val Ser Ser
        115                 120
```

<210> SEQ ID NO 18
<211> LENGTH: 119
<212> TYPE: PRT
<213> ORGANISM: Lama glama

<400> SEQUENCE: 18

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Arg Ser Ile Asn
            20                  25                  30

Ala Met Gly Trp Tyr Arg Gln Ala Pro Gly Lys Gln Arg Glu Phe Val
        35                  40                  45

Ala Arg Ile Thr Thr Gly Gly Thr Ile Gly Tyr Ala Asp Ser Val Lys
    50                  55                  60

Gly Arg Phe Thr Ile Ser Arg Asp Asn Ala Lys Asn Thr Met Tyr Leu
65                  70                  75                  80
```

-continued

Gln Met Asn Ser Leu Lys Pro Glu Asp Thr Ala Val Tyr Tyr Cys Asn
                85                  90                  95

Ala Asp Ile Gly Thr Trp Ser Ser Pro Tyr Tyr Trp Gly Gln Gly
            100                 105                 110

Thr Gln Val Thr Val Ser Ser
        115

<210> SEQ ID NO 19
<211> LENGTH: 122
<212> TYPE: PRT
<213> ORGANISM: Lama glama

<400> SEQUENCE: 19

Gln Val Gln Leu Gln Asp Ser Gly Gly Gly Leu Val Gln Ala Gly Gly
1               5                   10                  15

Ser Leu Arg Leu Ser Cys Ala Gly Val Gly Arg Thr Ile Ser Pro Tyr
            20                  25                  30

Asn Met Gly Trp Phe Arg Gln Ala Leu Gly Lys Glu Arg Asp Phe Val
        35                  40                  45

Ala Ala Ile Arg Trp Ser Gly Ser Asp Thr Asn Tyr Ala Asp Ser Val
50                  55                  60

Lys Gly Arg Phe Thr Ile Ser Arg Asp Asn Ala Arg Asn Thr Val Tyr
65                  70                  75                  80

Leu Gln Met Asn Asn Leu Asn Pro Glu Asp Thr Ala Val Tyr Tyr Cys
                85                  90                  95

Ala Ala Gly Gly Asp Val Phe Gly Ser Ala Leu Thr Tyr His His Trp
            100                 105                 110

Gly Gln Gly Thr Gln Val Thr Val Ser Ser
        115                 120

<210> SEQ ID NO 20
<211> LENGTH: 119
<212> TYPE: PRT
<213> ORGANISM: Lama glama

<400> SEQUENCE: 20

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Arg Ser Ile Asn
            20                  25                  30

Val Met Gly Trp Tyr Arg Gln Ala Pro Gly Lys Gln Arg Glu Leu Val
        35                  40                  45

Ala Leu Ile Thr Thr Gly Gly Ser Pro Ser Tyr Val Asp Ser Val Lys
50                  55                  60

Gly Arg Phe Thr Ile Ser Arg Asp Asn Ala Lys Ser Thr Ile Tyr Leu
65                  70                  75                  80

Gln Met Asp Ser Leu Lys Pro Glu Asp Thr Ala Val Tyr Tyr Cys Asn
                85                  90                  95

Ala Asp Ile Gly Thr Trp Ser Ser Pro Phe Tyr Tyr Trp Gly Gln Gly
            100                 105                 110

Thr Gln Val Thr Val Ser Ser
        115

<210> SEQ ID NO 21
<211> LENGTH: 122
<212> TYPE: PRT
<213> ORGANISM: Lama glama

```
<400> SEQUENCE: 21

Gln Val Gln Leu Gln Glu Ser Gly Gly Leu Val Gln Ala Gly Gly
1               5                   10                  15

Ser Leu Arg Leu Ser Cys Glu Gly Val Gly Arg Ser Ile Ser Pro Tyr
            20                  25                  30

Asn Met Gly Trp Phe Arg Gln Ala Pro Gly Lys Glu Arg Asp Phe Val
        35                  40                  45

Ala Ala Ile Arg Trp Ser Gly Ser Asp Thr Asn Tyr Ala Asp Ser Val
    50                  55                  60

Lys Gly Arg Phe Thr Ile Ser Arg Asp Asn Ala Arg Asn Thr Val Tyr
65                  70                  75                  80

Leu His Met Asn Ser Leu Asn Pro Glu Asp Thr Ala Val Tyr Tyr Cys
                85                  90                  95

Ala Ala Gly Gly Asp Val Ser Gly Ser Ala Leu Ser Tyr His Tyr Trp
            100                 105                 110

Gly Gln Gly Thr Gln Val Thr Val Ser Ser
        115                 120

<210> SEQ ID NO 22
<211> LENGTH: 23
<212> TYPE: DNA
<213> ORGANISM: Artificial
<220> FEATURE:
<223> OTHER INFORMATION: Synthetic sequence

<400> SEQUENCE: 22
gaggtbcarc tgcaggasag ygg                                        23

<210> SEQ ID NO 23
<211> LENGTH: 23
<212> TYPE: DNA
<213> ORGANISM: Artificial
<220> FEATURE:
<223> OTHER INFORMATION: Synthetic sequence

<400> SEQUENCE: 23
gaggtbcarc tgcaggastc ygg                                        23
```